US012668902B2

(12) United States Patent
Newman et al.

(10) Patent No.: US 12,668,902 B2
(45) Date of Patent: Jun. 30, 2026

(54) AIRLAID NONWOVEN

(71) Applicants: Fitesa (China) Airlaid Company Limited, Tianjin (CN); Fitesa Simpsonville, Inc., Simpsonville, SC (US)

(72) Inventors: Marc S. Newman, Simpsonville, SC (US); Yu Xin, Greer, SC (US); Jichun Ren, Tianjin (CN); Ding Hua, Tianjin (CN); Yijian Qu, Tianjin (CN)

(73) Assignees: Fitesa (China) Airlaid Company Limited, Tianjin (CN); Simpsonville, Inc.

(*) Notice: Subject to any disclaimer, the term of this patent is extended or adjusted under 35 U.S.C. 154(b) by 0 days.

(21) Appl. No.: 17/960,570

(22) Filed: Oct. 5, 2022

(65) Prior Publication Data

US 2023/0119760 A1 Apr. 20, 2023

Related U.S. Application Data

(60) Provisional application No. 63/256,406, filed on Oct. 15, 2021.

(51) Int. Cl.
*D04H 1/4382* (2012.01)
*A61F 13/535* (2006.01)
(Continued)

(52) U.S. Cl.
CPC ....... *D04H 1/43835* (2020.05); *A61F 13/535* (2013.01); *D04H 1/425* (2013.01);
(Continued)

(58) Field of Classification Search
CPC ........... D04H 1/43835; D04H 1/43838; D04H 1/43828; D04H 1/425; D04H 1/4291;
(Continued)

(56) References Cited

U.S. PATENT DOCUMENTS 6,479,415 B1 11/2002 Erspamer et al.
6,488,670 B1 12/2002 Schild et al.
(Continued)

FOREIGN PATENT DOCUMENTS

CN 1119581 A 4/1996
CN 1617696 A 5/2005
(Continued)

OTHER PUBLICATIONS

Wang et al., "Development of bamboo fiber-based composites," Advanced High Strength Natural Fibre Composites in Construction, pp. 235-255, 2017. (Year: 2017).*
(Continued)

*Primary Examiner* — Jeremy R Pierce

(57) ABSTRACT

Provided is a composite sheet material having a first layer and an airlaid nonwoven layer overlying the first layer wherein the airlaid nonwoven layer includes a blend of bamboo derived staple fibers and non-cellulose staple fibers, and in which the airlaid nonwoven layer includes a first surface disposed towards, and thermally bonded, to a surface of the first layer, and a second surface defining an outer surface of the composite sheet material.

21 Claims, 9 Drawing Sheets

(51) Int. Cl.

| | |
|---|---|
| ***D04H 1/425*** | (2012.01) |
| ***D04H 1/4291*** | (2012.01) |
| ***D04H 1/435*** | (2012.01) |
| ***D04H 1/724*** | (2012.01) |
| ***D04H 1/732*** | (2012.01) |
| ***D06N 3/00*** | (2006.01) |
| *A61F 13/15* | (2006.01) |
| *A61F 13/53* | (2006.01) |

(52) U.S. Cl.
CPC .......... *D04H 1/4291* (2013.01); *D04H 1/435* (2013.01); *D04H 1/43828* (2020.05); *D04H 1/43838* (2020.05); *D04H 1/724* (2013.01); *D04H 1/732* (2013.01); *D06N 3/0011* (2013.01); *A61F 2013/15406* (2013.01); *A61F 2013/530189* (2013.01); *A61F 2013/53024* (2013.01); *A61F 2013/530364* (2013.01); *A61F 2013/530379* (2013.01); *D06N 2201/0254* (2013.01); *D06N 2201/045* (2013.01); *D06N 2201/10* (2013.01); *D06N 2203/022* (2013.01); *D06N 2211/24* (2013.01); *D10B 2201/10* (2013.01); *D10B 2321/021* (2013.01); *D10B 2321/022* (2013.01); *D10B 2509/026* (2013.01)

(58) Field of Classification Search
CPC ........ D04H 1/435; D04H 1/724; D04H 1/732; A61F 13/535; D06N 3/0011
See application file for complete search history.

(56) References Cited

U.S. PATENT DOCUMENTS

| | | | |
|---|---|---|---|
| 2001/0039405 A1 | 11/2001 | Keuhn, Jr. et al. | |
| 2006/0287636 A1* | 12/2006 | Sakai | A61F 13/532 604/385.101 |
| 2008/0217809 A1 | 9/2008 | Zhao et al. | |
| 2009/0001118 A1 | 1/2009 | Habeck et al. | |
| 2009/0011188 A1 | 1/2009 | Yasumitsu et al. | |
| 2009/0023839 A1* | 1/2009 | Barnholtz | D04H 1/56 264/518 |
| 2009/0204095 A1 | 8/2009 | McDaniel | |
| 2012/0253310 A1* | 10/2012 | Hahn | A61F 13/496 156/227 |
| 2013/0101805 A1 | 4/2013 | Altshuler et al. | |
| 2014/0121621 A1 | 5/2014 | Kirby et al. | |
| 2015/0342802 A1 | 12/2015 | Caputi et al. | |
| 2017/0021051 A1* | 1/2017 | Richards | A61L 15/42 |
| 2020/0054782 A1* | 2/2020 | Chan | A61L 15/60 |
| 2020/0179188 A1* | 6/2020 | Lindner | A61F 13/531 |
| 2020/0197560 A1 | 6/2020 | Buchalter | |
| 2020/0316245 A1 | 10/2020 | Richards et al. | |
| 2020/0392658 A1 | 12/2020 | Ren et al. | |

FOREIGN PATENT DOCUMENTS

| | | | | |
|---|---|---|---|---|
| CN | 1732083 A | 2/2006 | | |
| CN | 1823189 A | 8/2006 | | |
| CN | 101085865 A | 12/2007 | | |
| CN | 101115453 A | 1/2008 | | |
| CN | 101528169 A | 9/2009 | | |
| CN | 101854820 A | 10/2010 | | |
| CN | 103042747 A | 4/2013 | | |
| CN | 203513968 U | 4/2014 | | |
| CN | 104540988 A | 4/2015 | | |
| CN | 104994821 B | 9/2019 | | |
| EP | 2852276 B1 | 7/2016 | | |
| EP | 3065537 B1 | 9/2017 | | |
| JP | 2003-113564 A | 4/2003 | | |
| JP | 2003-325411 A | 11/2003 | | |
| JP | 2007-031856 A | 2/2007 | | |
| JP | 2016-195753 A | 11/2016 | | |
| WO | 01/48291 A1 | 7/2001 | | |
| WO | 2013/056978 A2 | 4/2013 | | |
| WO | 2013175322 A1 | 11/2013 | | |
| WO | WO-2018197937 A1 * | 11/2018 | ....... | A61F 13/15658 |

OTHER PUBLICATIONS

International Search Report and Written Opinion for International Application No. PCT/US2022/045793, mailed Jan. 24, 2023 (11 pages).
International App. No. PCT/US2022/045793, Iprp dated Apr. 16, 2024.
Decision for a Patent for Japanese Patent Application No. 2019-559071 (3 pages).
English Translation of Notice of the Reasons for Rejection for Japanese Patent Application No. 2019-559071, dated Oct. 15, 2021 (9 pages).
European Search Report and Written Opinion for Application No. 17907418.2, dated Feb. 5, 2021 (12 pages).
Search Report for Chinese Application 2017800900488, dated Jul. 25, 2021.
Intention to Grant for Application No. 17907418.2, dated Nov. 22, 2021.
Notice of the Reasons for Rejection for Patent Application No. 2019-559071.
Translation of Search Report for Chinese Application 2017800900488, dated Jul. 25, 2021.
Second Office Action issued Jan. 24, 2022, CN Patent Application No. 201780090048.8 (14 pages).
First Examination Report dated Feb. 4, 2022, IN Patent Application No. 201917047813 (5 pages).
English Translation of Second Office Action issued Jan. 24, 2022, CN Patent Application No. 201780090048.8 (27 pages).

* cited by examiner

AIRLAID NONWOVEN

CROSS-REFERENCE TO RELATED APPLICATION

The present application claims priority of U.S. Provisional Application No. 63/256,406, filed Oct. 15, 2021, the contents of which are hereby incorporated by reference.

FIELD

The present invention relates generally to an airlaid nonwoven for use in absorbent articles, and more particularly, to an airlaid nonwoven comprising a blend of bamboo derived staple fibers and non-cellulose staple fibers.

BACKGROUND

Nonwovens made with a combination of various natural fibers and synthetic fibers are known for use in the manufacture of absorbent articles. Such absorbent articles may include disposable hygiene products, such as diapers, femcare sanitary products, adult incontinent products, wipes, and the like.

Despite significant developments in the manufacture and design of absorbent articles, there is still a need for absorbent articles having improved fluid management properties, reduced thickness, and increased flexibility. It is also important to utilize renewable/sustainable, bio-based feed stock content in order to reduce the amount of synthetic plastic materials introduced into the environment.

SUMMARY

Certain embodiments of the invention are directed to an airlaid nonwoven comprising a blend of non-cellulose staple fibers and bamboo derived staple fibers. Surprisingly, it has been found that using bamboo derived staple fibers in lieu of conventional wood pulp fibers provides notable improvements in desirable fluid management properties, such as the wicking rate and vertical wicking height, reduced thickness, and improved flexibility in comparison to an identical airlaid nonwoven comprising non-cellulose staple fibers and conventional wood pulp fibers.

In one embodiment, a composite sheet material comprises a first layer and an airlaid nonwoven layer overlying the first layer is provided wherein the airlaid nonwoven layer comprises a blend of bamboo derived staple fibers and non-cellulose staple fibers, and in which the airlaid nonwoven layer includes a first surface disposed toward, and thermally bonded, to a surface of the first layer, and a second surface defining an outer surface of the composite sheet material is provided.

In certain embodiments, the first layer is selected from the group consisting of spunbond nonwoven, meltblown nonwoven, spunlace nonwoven, carded nonwoven, airlaid nonwoven, cellulosic tissue, a spunbond-meltblown-spunbond composite, film, and combinations thereof. In a preferred embodiment, the first layer comprises a carded nonwoven fabric comprising a plurality of staple fibers that are air through bonded to each other form a coherent nonwoven fabric. In some embodiments, the first layer may comprise a composite structure, such as a meltblown-spunbond (MS) spunbond-meltblown-spunbond composite (SMS), a spunbond-meltblown-meltblown-spunbond composite (SMMS), and the like. Such composites can be used individually or in combination with one or more of the forementioned materials.

In some embodiments, the airlaid nonwoven layer comprises a plurality of airlaid layers that are thermally bonded to adjacent airlaid layers. For example, the airlaid nonwoven layer may comprise 2 to 10 successive airlaid layers. In one embodiment, the airlaid nonwoven layer comprises 3 to 6 airlaid layers.

In certain embodiments, the first layer comprises a carded nonwoven fabric comprising bicomponent staple fibers having a polyethyelene sheath and a polypropylene or polyethylene terephthalate core, and mixtures thereof. In some embodiments, the bicomponent staple fibers of the carded nonwoven fabric may have an average length from about 25 to 60 millimeters (mm).

In certain embodiments, the non-cellulose fibers of the airlaid nonwoven are bicomponent staple fibers having a polyethyelene sheath and a polypropylene or polyethylene terephthalate core, and mixtures thereof. In some embodiments, the non-cellulose fibers may have average lengths from about 0.8 to 10 millimeters (mm).

In certain embodiments, the first layer comprises a carded nonwoven fabric comprising polylactic acid (PLA) staple fibers, and the non-cellulose fibers of the airlaid nonwoven comprises PLA having a sheath/core configuration in which the sheath comprises PLA.

In certain embodiments, the first layer comprises a carded nonwoven fabric comprising a bio-based polymer.

In some embodiments, the non-cellulose staple fibers of the airlaid nonwoven layer comprise a bio-based polymer.

In some embodiments, the bio-based polymer of the first layer or the airlaid layer comprises an aliphatic polyester, a bio-based derived polyethylene, a bio-based derived polypropylene, bio-a based derived polyesters, such as bio-based derived polyethylene terephthalate (PET), and combinations thereof.

In some embodiments, the aliphatic polyester comprises polylactic acid (PLA), polybutylene succinate (PBS), and combinations and blends thereof.

In some embodiments, the basis weight of the composite sheet material is from about 25 to 400 $g/m^2$, such as from about 25 to 250 $g/m^2$ or 50 to 100 $g/m^2$.

In certain embodiments, the bamboo derived staple fibers have an average length from about 0.8 to 3.0 mm, and an average width from about 12 to 22 microns.

In some embodiments, the bamboo derived staple fibers have a length to width ratio that is from about 60 to 120.

In certain embodiments, a polymer coating layer is deposited overlying a surface of the airlaid nonwoven layer, wherein the polymer coating comprises an ethylene vinyl acetate, ethylene acrylate, polyacrylate, phenylethylene, butadiene, styrene butadiene-acrylate, polyvinyl alcohol, bio-based latex, and mixtures thereof.

In some embodiments, an add-on dried weight of the polymer coating is from about 1.5 to 4 weight percent, based on the total weight of the composite sheet material.

In some embodiments, the composite sheet material comprises a carded nonwoven fabric comprised of staple fibers and at least one airlaid nonwoven layer overlying the carded nonwoven fabric, and wherein the composite sheet material exhibits a basis weight ranging from about 60 to 100 $g/m^2$, and the composite sheet material has a thickness ranging from about 0.5 to 3.0 mm, a CD stiffness ranging from about 5 to 15 mN/cm and a MD stiffness ranging from about 20 to 50 mN/cm.

In certain embodiments, the composite sheet material exhibits a wicking rate from about 30 to 50 mm/15 sec, and a vertical fluid wicking height from about 30 to 70 mm.

In some embodiments, the composite sheet material comprises a carded nonwoven fabric comprised of staple fibers and at least one airlaid nonwoven layer overlying the carded nonwoven fabric, and wherein the composite sheet material exhibits a basis weight ranging from about 60 to 100 g/$m^2$, and the composite sheet material exhibits a thickness ranging from about 1.25 to 1.40 mm, a CD stiffness ranging from about 6 to 14 mN/cm, a MD stiffness ranging from about 25 to 40 mN/cm, a wicking rate from about 32 to 40 mm/15 sec, and a vertical fluid wicking height from about 35 to 65 mm.

In certain embodiments, the composite sheet exhibits an increase in vertical wicking height ranging from 50 to 150% and an increase in wicking rate ranging from 40 to 120% in comparison to an identical composite sheet material in which the airlaid nonwoven layer comprises staple fibers comprising conventional wood pulp fibers in lieu of bamboo derived staple fibers.

In certain embodiments, the composite sheet exhibits a decrease in MD stiffness ranging from 10 to 50%, and a decrease in CD stiffness ranging from 10 to 60% in comparison to an identical composite sheet material in which the airlaid nonwoven comprises staple fibers comprising conventional wood pulp fibers in lieu of bamboo derived staple fibers.

In some embodiments, the airlaid nonwoven comprises one or more airlaid layers, and at least one of the airlaid layers comprises a super absorbent polymer.

In certain embodiments, the airlaid nonwoven layer is thermally bonded via air through bonding and the first layer is bonded to the overlying airlaid nonwoven layer via air through bonding.

In certain embodiments, the airlaid layer includes staple fibers comprising conventional wood pulp fibers. In one such embodiment, the amount of conventional wood pulp fibers in the airlaid layer is from about 10 to 90 weight percent, based on a combined weight of the conventional wood pulp fibers and the bamboo derived staple fibers.

In certain embodiments, the composite sheet material may comprise a component of an absorbent article. Embodiments of the invention are also directed to the use of the composite sheet material in an absorbent article.

A further aspect of the invention is also directed to a method of making a composite sheet comprising the steps of providing a first layer of a sheet material; depositing a first airlaid layer onto a surface of the first layer to form a composite sheet, the first airlaid layer comprising a mixture of bamboo derived staple fibers and non-cellulose staple fibers; and air through bonding the composite sheet with heated gas to cause a polymer of the non-cellulose staple fibers to melt and fuse with adjacent fibers, wherein non-cellulose staple fibers of the air laid layer are bonded to each other, the bamboo derived staple fibers, and the first layer.

In certain embodiments, the method further comprises successively depositing a plurality of airlaid layers onto the first airlaid layer. In some embodiments, the composite sheet comprises from 2 to 10 airlaid layers successively deposited overlying the carded nonwoven fabric.

In some embodiments of the method, the first layer comprises a carded nonwoven fabric comprising bicomponent staple fibers having a polyethyelene sheath and a polypropylene or polyethylene terephthalate core, and mixtures thereof, and the non-cellulose fibers of the airlaid nonwoven comprise bicomponent staple fibers have a polyethyelene sheath and a polypropylene or polyethylene terephthalate core, and mixtures thereof.

In some embodiments of the method, the bicomponent staple fibers of the carded nonwoven fabric have a length from about 25 to 60 millimeters (mm), and the non-cellulose fibers of the airlaid nonwoven have a length from about 0.8 to 10 millimeters (mm).

In certain embodiments of the method, the carded nonwoven fabric comprises polylactic acid (PLA) staple fibers, and the non-cellulose fibers comprise PLA bicomponent fibers having a sheath/core structure in which the sheath comprises PLA.

In some embodiments, the method comprising a step of depositing a coating layer of a polymeric latex on a surface an outermost airlaid layer, and then heating the composite sheet material to a temperature sufficient to cure and dry the polymeric latex.

In some embodiments of the method, the method further comprise a step of adding a super absorbent polymer to at least one layer of the airlaid nonwoven layer.

In certain embodiments, a method of making a composite sheet is provided comprising the steps of

- providing a first layer of a sheet material;
- depositing a first airlaid layer onto a surface of the first layer to form a composite sheet, the first airlaid layer comprising a mixture of bamboo derived staple fibers and non-cellulose staple fibers; and
- air through bonding the composite sheet with heated gas to cause a polymer of the non-cellulose staple fibers to melt and fuse with adjacent fibers, wherein non-cellulose staple fibers of the air laid layer are bonded to each other, the bamboo derived staple fibers, and the first layer.

In certain embodiments of the method, the method includes successively depositing a plurality of airlaid layers onto the first airlaid layer.

In some embodiments of the method, the composite sheet comprises from 2 to 10 airlaid layers successively deposited overlying the carded nonwoven fabric.

In some embodiments of the method, the first layer is selected from the group consisting of spunbond nonwoven, meltblown nonwoven, spunlace nonwoven, carded nonwoven, airlaid nonwoven, cellulosic tissue paper, film, and combinations thereof.

In some embodiments of the method, the first layer comprises a carded nonwoven fabric comprising a plurality of staple fibers that are air through bonded to each other form a coherent nonwoven fabric.

In some embodiments of the method, the airlaid nonwoven layer comprises a plurality of airlaid layers that are thermally bonded to adjacent airlaid layers.

In some embodiments of the method, the airlaid nonwoven layer comprises 2 to 10 airlaid layers, and in particular from 3 to 6 airlaid layers.

In some embodiments of the method, the first layer comprises a carded nonwoven fabric comprising bicomponent staple fibers having a polyethyelene sheath and a polypropylene or polyethylene terephthalate core, and mixtures thereof.

In some embodiments of the method, the non-cellulose fibers are bicomponent staple fibers having a polyethyelene sheath and a polypropylene or polyethylene terephthalate core, and mixtures thereof.

In some embodiments of the method, the first layer comprises a carded nonwoven fabric comprising a bio-based polymer.

In some embodiments of the method, the non-cellulose staple fibers of the airlaid nonwoven layer comprise a bio-based polymer.

In some embodiments of the method, the bio-based polymer comprises an aliphatic polyester, a bio-based derived polyethylene, a bio-based derived polypropylene, bio-a based derived polyesters, such as bio-based derived polyethylene terephthalate (PET), and combinations thereof.

In some embodiments of the method, the aliphatic polyester comprises polylactic acid (PLA), polybutylene succinate (PBS), and combinations and blends thereof.

In some embodiments of the method, the basis weight of the composite sheet material is from about 25 to 250 $g/m^2$.

In some embodiments of the method, the bamboo derived staple fibers have an average length from about 0.8 to 3.0 mm, and an average width from about 12 to 22 microns.

In some embodiments of the method, the bamboo derived staple fibers have a length to width ratio that is from about 60 to 120.

In some embodiments of the method, the method further comprises a step of depositing a polymer coating layer overlying a surface of the airlaid nonwoven layer, said polymer coating comprising an ethylene vinyl acetate, ethylene acrylate, polyacrylate, phenylethylene, butadiene, styrene butadiene-acrylate, polyvinyl alcohol, bio-based latex, and mixtures thereof.

In some embodiments of the method, an add-on dried weight of the polymer coating is from about 1.5 to 4 weight percent, based on the total weight of the composite sheet material.

In some embodiments of the method, the composite sheet material exhibits a thickness ranging from about 0.5 to 3.0 mm, a CD stiffness ranging from about 5 to 15 mN/cm and a MD stiffness ranging from about 20 to 50 mN/cm.

In some embodiments of the method, wherein the composite sheet exhibits a wicking rate from about 30 to 50 mm/15 sec, and a vertical fluid wicking height from about 30 to 70 mm.

In some embodiments of the method, the composite sheet exhibits a thickness ranging from about 1.25 to 1.40 mm, a CD stiffness ranging from about 6 to 14 mN/cm, a MD stiffness ranging from about 25 to 40 mN/cm, a wicking rate from about 32 to 40 mm/15 sec, and a vertical fluid wicking height from about 35 to 65 mm.

In some embodiments of the method, the composite sheet exhibits an increase in vertical wicking height ranging from 50 to 150% and an increase in wicking rate ranging from 40 to 120 in comparison to an identical composite sheet material in which the airlaid nonwoven layer comprises staple fibers comprising conventional wood pulp fibers in lieu of bamboo derived staple fibers.

In some embodiments of the method, the composite sheet exhibits a decrease in MD stiffness ranging from 10 to 50%, and a decrease in CD stiffness ranging from 10 to 60% in comparison to an identical composite sheet material in which the airlaid nonwoven comprises staple fibers comprising conventional wood pulp fibers in lieu of bamboo derived staple fibers.

In some embodiments of the method, the airlaid nonwoven comprises one or more airlaid layers, and at least one of the airlaid layers comprises a super absorbent polymer.

In some embodiments of the method, the airlaid nonwoven layer is thermally bonded via air through bonding and the first layer is bonded to the overlying airlaid nonwoven layer via air through bonding.

In a further aspect, embodiments of the invention are directed to an absorbent core of an absorbent article in which the core comprises bamboo derived staple fibers.

In one such aspect, the absorbent core comprises a first layer of fibers bonded together to form a coherent web; and an airlaid nonwoven layer overlying the first layer, the airlaid nonwoven layer comprising a blend of bamboo derived staple fibers and non-cellulose staple fibers, the airlaid nonwoven layer comprising a first surface disposed towards, and thermally bonded, to a surface of the first layer, and a second surface defining an outer surface of the composite sheet material.

In some aspects of the absorbent core, the first layer is selected from the group consisting of spunbond nonwoven, meltblown nonwoven, spunlace nonwoven, carded nonwoven, airlaid nonwoven, cellulosic tissue paper, and combinations thereof.

In some aspects of the absorbent core, the first layer comprises a carded nonwoven fabric comprising a plurality of staple fibers that are air through bonded to each other form a coherent nonwoven fabric.

In some aspects of the absorbent core, the airlaid nonwoven layer comprises a plurality of airlaid layers that are thermally bonded to adjacent airlaid layers.

In some aspects of the absorbent core, the airlaid nonwoven layer comprises 2 to 10 airlaid layers, and in particular from 3 to 6 airlaid layers.

In some aspects of the absorbent core, the first layer comprises a carded nonwoven fabric comprising bicomponent staple fibers having a polyethyelene sheath and a polypropylene or polyethylene terephthalate core, and mixtures thereof.

In some aspects of the absorbent core, the non-cellulose fibers are bicomponent staple fibers having a polyethyelene sheath and a polypropylene or polyethylene terephthalate core, and mixtures thereof.

In some aspects of the absorbent core, first layer comprises a carded nonwoven fabric comprising a bio-based polymer.

In some aspects of the absorbent core, the non-cellulose staple fibers of the airlaid nonwoven layer comprise a bio-based polymer.

In some aspects of the absorbent core, the bio-based polymer comprises an aliphatic polyester, a bio-based derived polyethylene, a bio-based derived polypropylene, bio-a based derived polyesters, such as bio-based derived polyethylene terephthalate (PET), and combinations thereof.

In some aspects of the absorbent core, the aliphatic polyester comprises polylactic acid (PLA), polybutylene succinate (PBS), and combinations and blends thereof.

In some aspects of the absorbent core, the basis weight of the composite sheet material is from about 25 to 400 $g/m^2$.

In some aspects of the absorbent core, the bamboo derived staple fibers have an average length from about 0.8 to 5.0 mm, such as from about 1.0 to 3.0 mm, and an average width from about 12 to 22 microns.

In some aspects of the absorbent core, the bamboo derived staple fibers have a length to width ratio that is from about 60 to 120.

In some aspects of the absorbent core, the core exhibits a thickness ranging from about 0.5 to 5.0 mm, such as from about 0.5 to 3.0 mm, a CD stiffness ranging from about 5 to 15 mN/cm and a MD stiffness ranging from about 20 to 50 mN/cm.

In some aspects of the absorbent core, the core exhibits a wicking rate from about 30 to 50 mm/15 sec, and a vertical fluid wicking height from about 30 to 70 mm.

In some aspects of the absorbent core, the core exhibits a thickness ranging from about 1.25 to 1.40 mm, a CD stiffness ranging from about 6 to 14 mN/cm, a MD stiffness ranging from about 25 to 40 mN/cm, a wicking rate from about 32 to 40 mm/15 sec, and a vertical fluid wicking height from about 35 to 65 mm.

In some aspects of the absorbent core, the core exhibits an increase in vertical wicking height ranging from 50 to 150% and an increase in wicking rate ranging from 40 to 120 in comparison to an identical absorbent core material in which the airlaid nonwoven layer comprises staple fibers comprising conventional wood pulp fibers in lieu of bamboo derived staple fibers.

In some aspects of the absorbent core, the core exhibits a decrease in MD stiffness ranging from 10 to 50%, and a decrease in CD stiffness ranging from 10 to 60% in comparison to an identical absorbent core material in which the airlaid nonwoven comprises staple fibers comprising conventional wood pulp fibers in lieu of bamboo derived staple fibers.

In some aspects of the absorbent core, the airlaid nonwoven comprises one or more airlaid layers, and at least one of the airlaid layers comprises a super absorbent polymer.

In some aspects of the absorbent core, the airlaid nonwoven layer is thermally bonded via air through bonding and the first layer is bonded to the overlying airlaid nonwoven layer via air through bonding.

In some aspects of the absorbent core, the core comprises from about 10 to 90 weight percent of bamboo derived staple fibers and from about 10 to 90 weight percent of staple fibers comprising conventional wood pulp fibers.

In some aspects of the absorbent core, the fibers of the core are bonded with a polymeric material comprising an ethylene vinyl acetate, ethylene acrylate, polyacrylate, phenylethylene, butadiene, styrene butadiene-acrylate, polyvinyl alcohol, bio-based latex, and mixtures thereof.

In some aspects of the absorbent core, an add-on dried weight of the polymer material is from about 1.5 to 5 weight percent, based on the total weight of the absorbent core.

In some aspects of the absorbent core, the core further comprises a super absorbent polymer.

In some aspects of the absorbent core, the basis weight of the composite sheet material is from about 25 to 400 $g/m^2$.

In some aspects of the absorbent core, the bamboo derived staple fibers have an average length from about 0.8 to 3.0 mm, and an average width from about 12 to 22 microns.

In some aspects of the absorbent core, the bamboo derived staple fibers have a length to width ratio that is from about 60 to 120.

In some aspects of the absorbent core, the absorbent core further comprising a tissue layer.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
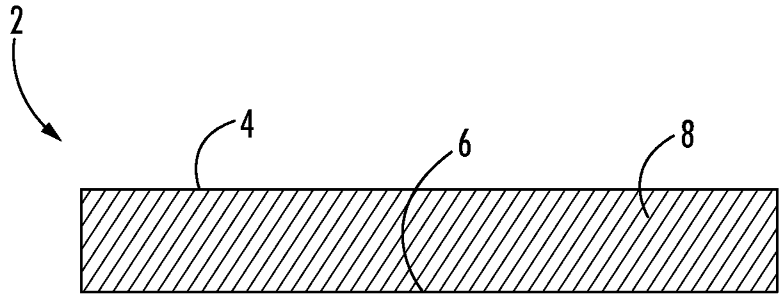
FIG. 1 is a cross-sectional side view of an airlaid nonwoven in accordance with at least one embodiment of the present invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

Definitions

For the purposes of the present application, the following terms shall have the following meanings:

The term "fiber" can refer to a fiber of finite length or a filament of infinite length.

The term "staple fiber" refers to a fibers of finite length. In general staple fibers may have a length from about 2 to 200 millimeters (mm).

As used herein, the term "monocomponent" refers to fibers formed from one polymer or formed from a single blend of polymers. Of course, this does not exclude fibers to which additives have been added for color, anti-static properties, lubrication, hydrophilicity, liquid repellency, etc.

As used herein, the term "multicomponent" refers to fibers formed from at least two polymers (e.g., bicomponent fibers) that are extruded from separate extruders. The at least two polymers can each independently be the same or different from each other, or be a blend of polymers. The polymers are arranged in substantially constantly positioned distinct zones across the cross-section of the fibers. The components may be arranged in any desired configuration, such as sheath-core, side-by-side, segmented pie, island-in-the-sea, and so forth. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference.

As used herein, the terms "nonwoven," "nonwoven web" and "nonwoven fabric" refer to a structure or a web of material which has been formed without use of weaving or knitting processes to produce a structure of individual fibers or threads which are intermeshed, but not in an identifiable, repeating manner. Nonwoven webs have been, in the past, formed by a variety of conventional processes such as, for example, meltblown processes, spunbond processes, and staple fiber carding processes.

As used herein, the term "carded fabric" refers to a nonwoven fabric comprising staple fibers that are predominantly aligned and oriented in the machine direction using a carding process.

As used herein, the term "conventional pulp fiber" refers to cellulose fibers typically derived from wood pulp, such as hardwood and softwood pulps, and do not include fibers derived from bamboo pulp.

As used herein, the term "meltblown" refers to a process in which fibers are formed by extruding a molten thermoplastic material through a plurality of fine, usually circular, die capillaries into a high velocity gas (e.g. air) stream which attenuates the molten thermoplastic material and forms fibers, which can be to microfiber diameter. Thereafter, the meltblown fibers are carried by the gas stream and are deposited on a collecting surface to form a web of random meltblown fibers. Such a process is disclosed, for example, in U.S. Pat. No. 3,849,241 to Buntin et al.

As used herein, the term "machine direction" or "MD" refers to the direction of travel of the nonwoven web during manufacturing.

As used herein, the term "cross direction" or "CD" refers to a direction that is perpendicular to the machine direction and extends laterally across the width of the nonwoven web.

As used herein, the term "spunbond" refers to a process involving extruding a molten thermoplastic material as filaments from a plurality of fine, usually circular, capillaries of a spinneret, with the filaments then being attenuated and drawn mechanically or pneumatically. The filaments are deposited on a collecting surface to form a web of randomly arranged substantially continuous filaments which can thereafter be bonded together to form a coherent nonwoven fabric. The production of spunbond non-woven webs is illustrated in patents such as, for example, U.S. Pat. Nos. 3,338,992; 3,692,613; 3,802,817; 4,405,297; and 5,665,300. In general, these spunbond processes include extruding the filaments from a spinneret, quenching the filaments with a flow of air to hasten the solidification of the molten filaments, attenuating the filaments by applying a draw tension, either by pneumatically entraining the filaments in an air stream or mechanically by wrapping them around mechanical draw rolls, depositing the drawn filaments onto a foraminous collection surface to form a web, and bonding the web of loose filaments into a nonwoven fabric. The bonding can be any thermal or chemical bonding treatment, with thermal point bonding being typical.

As used herein, the term "air through thermal bonding" involves passing a material such as one or more webs of fibers to be bonded through a stream of heated gas, such as air, in which the temperature of the heated gas is above the softening or melting temperature of at least one polymer component of the material being bonded. Air through thermal bonding may involve passing a material through a heated oven.

As used herein, the term "thermal point bonding" involves passing a material such as one or more webs of fibers to be bonded between a heated calender roll and an anvil roll. The calender roll is typically patterned so that the fabric is bonded in discrete point bond sites rather than being bonded across its entire surface.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material, including isotactic, syndiotactic and random symmetries.

The term "composite", as used herein, may be a structure comprising two or more layers, such as a film layer and a fiber layer or a plurality of fiber layers joined together. The two layers of a composite structure may be joined together such that a substantial portion of their common X-Y plane interface are joined with each other.

Unless otherwise apparent from the context, the term "about" encompasses values within a standard margin of error of measurement (e.g., SEM) of a stated value or variations±0.5%, 1%, 5%, or 10% from a specified value.

Embodiments of the invention are directed to a sheet material comprising an airlaid nonwoven that is a blend of non-cellulose staple fibers and bamboo-derived pulp fibers. The sheet material in accordance with one or more embodiments of the invention is particularly useful in the manufacture of absorbent articles, and in particular, disposable feminine hygiene products and incontinence products.

I. Airlaid Nonwoven Fabric

With reference to FIG. 1, an airlaid nonwoven is shown and broadly designated by reference character 2. The airlaid nonwoven 2 comprises a plurality of non-cellulose staple fibers and bamboo derived staple fibers that are blended in a single layer 8. The single layer 8 includes an upper surface 4 and a lower surface 6. The non-cellulose staple fibers and the bamboo derived staple fibers may be homogeneously or heterogeneously blended together throughout the airlaid nonwoven.

As discussed in greater detail below, it has been discovered that airlaid nonwovens comprising bamboo derived staple fibers in lieu of conventional wood pulp fibers provides improvements in certain fluid handling properties as well as a decrease in overall thickness of the airlaid nonwoven in comparison to a similarly prepared airlaid nonwoven comprising conventional pulp fibers. In addition, airlaid nonwovens in accordance with certain embodiments of the invention exhibits improvements with respect to flexibility in comparison to a similarly prepared fabrics comprising of conventional pulp fibers. As such, airlaid nonwovens in accordance with embodiments of the invention are particularly useful in a variety of applications in the manufacture of absorbent articles. By "similarly prepared" or "similar airlaid nonwoven" it is meant that the airlaid nonwovens have identical chemistry or substantially identical chemistry and have been processed under similar or identical processing conditions, with the exception of the substitution of bamboo derived staple fibers used in place of conventional pulp fibers.

In certain embodiments, airlaid nonwovens in accordance with embodiment the invention exhibit a decrease in thickness (caliper) ranging from 10 to 60%, and in particular, from about 20 to 50%, and more particularly, from 25 to 45% in comparison to a similar airlaid nonwoven in which the similar airlaid nonwoven comprises staple fibers comprising conventional wood pulp fibers in lieu of bamboo derived staple fibers.

In certain embodiments, airlaid nonwovens in accordance with embodiments of the invention exhibit a decrease in MD stiffness ranging from 10 to 50%, and in particular, from about 15 to 35%, and more particularly, from 20 to 30% in comparison to a similar airlaid nonwoven in which the similar airlaid nonwoven comprises staple fibers comprising conventional wood pulp fibers in lieu of bamboo derived staple fibers.

In certain embodiments, airlaid nonwovens in accordance with embodiments of the invention exhibit a decrease in CD stiffness ranging from 10 to 60%, and in particular, from about 20 to 50%, and more particularly, from 25 to 45% in comparison to a similar airlaid nonwoven in which the similar airlaid nonwoven comprises staple fibers comprising conventional wood pulp fibers in lieu of bamboo derived staple fibers.

Advantageously, a reduction in stiffness of the airlaid nonwoven helps to provide a reduction in the overall stiffness in the absorbent article comprising the airlaid nonwoven, which results in an increased flexibility in the absorbent article. Reductions in thickness and increases in flexibility are generally desirable because they help to improve the comfort and wearability of the absorbent article as well as providing an article having improved discreetness.

Further, it has been observed that airlaid nonwovens in accordance with certain embodiments of the invention exhibit improved flexibility (e.g., reduced stiffness) in comparison to a similar airlaid nonwoven in which the similar airlaid nonwoven comprises staple fibers comprising conventional wood pulp fibers in lieu of bamboo derived staple fibers.

Advantageously, these improvements associated with the use of bamboo derived staple fibers are provided without significantly sacrificing other desirable fluid management properties of the airlaid nonwoven, such as fluid acquisition time, fluid retention, and fluid absorption.

In addition, airlaid nonwovens in accordance with certain embodiments of the invention exhibit improved wicking properties (capillary action of the fluid moving through the component) in comparison to a similar airlaid nonwoven in which the similar airlaid nonwoven comprises staple fibers comprising conventional wood pulp fibers in lieu of bamboo derived staple fibers.

In certain embodiments, airlaid nonwovens in accordance with embodiments of the invention exhibit an increase in vertical wicking height ranging from 50 to 150%, and in particular, from about 75 to 140%, and more particularly, from 90 to 130% in comparison to a similar airlaid nonwoven in which the similar airlaid nonwoven comprises staple fibers comprising conventional wood pulp fibers in lieu of bamboo derived staple fibers.

In certain embodiments, airlaid nonwovens in accordance with the invention exhibit an increase in wicking rate ranging from 40 to 120%, and in particular, from about 50 to 110%, and more particularly, from 60 to 100% in comparison to a similar airlaid nonwoven in which the similar airlaid nonwoven comprises staple fibers comprising conventional wood pulp fibers in lieu of bamboo derived staple fibers. In some embodiments, airlaid nonwovens in accordance with embodiments of the invention exhibit an increase in wicking rate ranging from 75 to 95%, in comparison to a similar airlaid nonwoven in which the similar airlaid nonwoven comprises staple fibers comprising conventional wood pulp fibers in lieu of bamboo derived staple fibers.

In certain embodiments, the airlaid nonwoven may also include antibacterial properties due to naturally occurring antibacterial agents present in bamboo.

The fibers of the airlaid nonwoven may be bonded to adjacent fibers using thermal, ultrasonic, mechanical, and adhesive bonding. In some embodiments, the airlaid layers may be bonded via hydrogen bonding. In certain embodiments, the airlaid nonwoven fabric is thermally bonded by passing the airlaid nonwoven through a thermal bonding unit in which the airlaid nonwoven is subjected to a heated gas, such as air, at a temperature above the melting point of at least one polymeric material of the airlaid nonwoven. In a preferred embodiment, the airlaid nonwoven is passed through an air through thermal bonding unit in which a stream of heated gas, such as air, is above the temperature of the softening or melting temperature of at least one polymer component of the airlaid nonwoven.

In some embodiments, the fibers of the airlaid nonwoven may be bonded via thermal calender bonding. In certain other embodiments, the fibers of the airlaid nonwoven are not subjected to thermal calender bonding. In certain embodiments, the fibers of the airlaid nonwoven are not bonded via hydraulic entanglement and are characterized by the absence of a hydraulic entanglement process in the bonding of the fibers.

Figure 2:
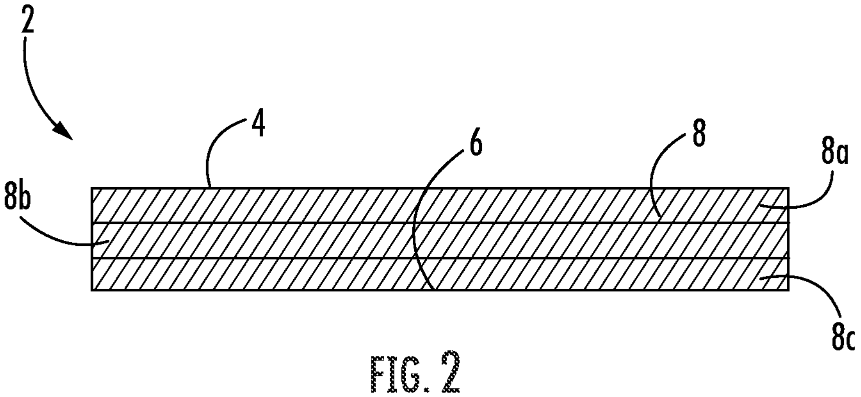
FIG. 2 is a cross-sectional side view of an airlaid nonwoven having multiple airlaid layers overlying each other.

In some embodiments, the airlaid nonwoven 2 may comprise one or more airlaid layers. In this regard, FIG. 2 illustrates an embodiment of the invention in which the airlaid nonwoven 2 comprises a plurality of airlaid layers (layers 8*a*, 8*b*, and 8*c*) that are formed overlying one another. Preferably, each of the airlaid layers are adjacent to, and in direct contact with, immediately adjacent layers of the sheet material so that adjacent layers are in fluid communication with respect to each other. In embodiments comprising multiple airlaid nonwoven layers, adjacent layers may be bonded to each other using the previously mentioned bonding techniques. Preferably, the plurality of airlaid layers are thermally bonded to each other by passing the airlaid nonwoven through an air through bonding unit.

Generally, the airlaid nonwoven has a basis weight ranging from about 25 to 400 (g/m$^2$) depending on the intended application. In certain embodiments, the airlaid nonwoven may have a basis weight ranging from about 40 to 200 g/m$^2$, and more particularly, from about 50 to 100 g/m$^2$. In a preferred embodiment, the airlaid nonwoven has a basis weight that is about 35 to 80 g/m$^2$.

The thickness of the airlaid nonwoven may range from about 0.4 to 4 mm, and in particular, from about 0.7 to 3 mm, and more particularly, from about 0.7 to 2 mm. In a preferred embodiment, the airlaid nonwoven has a thickness that is about 0.8 to 1.5 mm.

A. Bamboo Derived Staple Fibers

Bamboo derived staple fibers may comprise treated and untreated bamboo pulp. Typical pulping methods for obtaining bamboo derived staple fibers may include chemical pulping, chemi-mechanical pulp, thermal mechanical pulp, and mixtures thereof.

A wide variety of different bamboo species may be used. Both running bamboo and clumping bamboo may be utilized. In certain embodiments, the bamboo derived staple fibers may be derived from clumping bamboo.

Typically, bamboo derived staple fibers for use in certain embodiments of the invention exhibit average lengths ranging from 0.5 to 4.5 mm (e.g., from 0.5 to 3 mm), and in particular, from about 0.7 to 2.5 mm, such as from about 0.8 to 2.2 mm, and more particularly, from about 1.2 to 2.0 mm. In a preferred embodiment, the bamboo derived staple fibers exhibit average lengths ranging from 1.6 to 1.8 mm.

In certain embodiments, the bamboo derived staple fibers exhibit widths (cross-section diameters) ranging from 10 to 30 microns, such as from 10 to 26 microns, and in particular, from about 12 to 22 microns, and more particularly, from about 14 to 20 microns. In a preferred embodiment, the bamboo derived staple fibers exhibit widths ranging from 16 to 18 microns.

In some embodiments, the bamboo derived staple fibers exhibit a length to width ratio that is from about 130 to 50, and in particular, from about 120 to 60 or 110 to 70, and more particularly, from about 80 to 100. In a preferred embodiment, the bamboo derived staple fibers exhibit a length to width ratio that is from about 92 to 98.

The amount of bamboo derived staple fibers in the airlaid nonwoven is typically from about 20 to 95 weight %, and in particular, from about 30 to 75 weight percent, based on the total weight of the airlaid nonwoven. In a preferred embodiment, the amount of bamboo derived staple fibers in the airlaid nonwoven is from about 40 to 60 weight %, based on the total weight of the airlaid nonwoven.

In certain embodiments, the cellulose portion of the airlaid nonwoven comprises 100% of bamboo derived staple fibers. In some embodiments, the cellulose portion of the airlaid nonwoven comprises at least 95%, such as at 96%, at least 97%, at least 98%, and at least 99% of bamboo derived staple fibers.

B. Non-Cellulose Staple Fibers

The non-cellulose staple fibers of the airlaid nonwoven typically have lengths ranging from about 0.8 to 15 mm, and in particular, from about 3 to 10 mm, and more particularly, from about 3 to 6 mm.

Suitable materials for the non-cellulose staple fibers for use in the airlaid nonwoven may comprise monocomponent or multicomponent fibers, or mixtures of moncomponent and multicomponent fibers. In a preferred embodiment, the non-cellulose staple fibers of the airlaid nonwoven comprise bicomponent fibers having a sheath/core configuration.

In one embodiment, the staple fibers comprise bicomponent fibers have a sheath/core configuration. Examples of bicomponent fibers include side-by-side, islands in the sea, and sheath/core arrangements. Preferably, the fibers have a sheath/core structure in which the sheath comprises a first polymer component, and the core comprises a second polymer component. In this arrangement, the polymers of the first and second polymer components may be the same or different from each other. For example, in one embodiment, the sheath comprises a first polymer component, and the core comprises a second polymer component that is different or the same as the first polymer component. In a preferred embodiment, the first and second polymer components of the bicomponent fibers are different from each other.

In some embodiments the staple fibers of the airlaid nonwoven may have a sheath/core configuration in which the core is centered relative to the sheath. Alternatively, the core may be present in an off-set configuration relative to the sheath. In this configuration, the core not centrally aligned relative to the sheath. As a result, when heat is applied, such as during bonding, the fibers will have a tendency to curl or crimp, which in turn may help provide loft to the airlaid nonwoven.

In one embodiment, the first polymer component of the sheath comprises a polymer having a lower melting temperature than that of the second polymer component comprising the core. The lower melting polymer of the sheath will promote bonding while the polymer component of the core having a higher melting temperature will provide strength to the fiber and thus to the final bonded nonwoven.

Generally, the weight percentage of the sheath to that of the core in the fibers may vary widely depending upon the desired properties of the nonwoven fabric. For example, the weight ratio of the sheath to the core may vary between about 10:90 to 90:10, and in particular from about 20:80 to 80:20. In a preferred embodiment, the weight ratio of the sheath to the core is about 60:40 to 40:60, with a weight ratio of about 50:50 being preferred.

A wide variety of polymers may be used for preparing non-cellulose staple fibers for use in the airlaid nonwoven. Examples of suitable fibers include may include polyolefins, such as polypropylene and polyethylene, and copolymers thereof, polyesters, such as polyethylene terephthalate (PET), polytrimethylene terephthalate (PTT), and polybutylene terephthalate (PBT), nylons, polystyrenes, copolymers, and blends thereof, and other synthetic polymers that may be used in the preparation of fibers. In one embodiment, the non-cellulose staple fibers have a sheath/core configuration comprising a polyethylene sheath and a polypropylene core. In other embodiments, the staple fibers may have a sheath/core configuration comprising a polyethylene sheath and a polyester core, such as a core comprising polyethylene terephthalate.

In some embodiments, the non-cellulose staple fibers may comprise a blend of fibers such as a blend of bicomponent staple fibers having a polyethylene sheath and a polyethylene terephthalate core, and bicomponent staple fibers having a polyethylene sheath and a polypropylene core. In one embodiment, the fibers of the airlaid nonwoven may include eccentric bicomponent staple fibers having a polyethylene sheath and a polyethylene terephthalate core, a fineness of 4.3 dtex, and an average length of 3 to 6 mm. Examples of such fibers are available from Indorama Polyester Industries Public Company Limited under the product name TS47.

In one embodiment, the non-cellulose staple fibers of the airlaid nonwoven may comprise bicomponent staple fibers having a polyethylene sheath and a polyethylene terephthalate core. One such example is bicomponent staple fiber having a fineness of 2.2 dtex, and an average length of 3 mm, which are available from Toray Chemical Korea Inc. under the product name EZBON A (UN-204). A further example is an eccentric bicomponent staple fibers having a polyethylene sheath and a polyethylene terephthalate core. Such a fiber is available from IndoramaPolyester Industries Public Company Limited under the product name TS47 (a fineness of 4.3 dtex, and an average length of 3 mm). Another example is a bicomponent staple fibers having a polyethylene sheath and a polyethylene terephthalate core is available from Trevira under the product designation T255 staple fibers. These staple fibers have a fineness of 4.3 dtex, and an average length of 3 mm.

In another embodiment, the non-cellulose staple fibers may comprise bicomponent staple fibers having a polyethylene sheath and a polypropylene core. One such example is a staple fiber having a fineness of 4.0 dtex, and an average length of 4 mm, which are available from Yangzhou Petrochemical Co. Ltd. under the product name Y116. Another example of bicomponent staple fibers having a polyethylene sheath and a polypropylene core, a denier of 6.0, and an average length of 5 mm, are available from JiangNan High Polymer Fiber under the product designation JNGX-PZ11-6*51L.

In some embodiments, the non-cellulose fibers may comprise blends of fibers, such as blends comprising bicomponent PE/PET and PE/PP staple fibers.

The above noted polymers are generally considered to be derived from synthetic sources, such as a petroleum derived polymer. In some embodiments, it may be desirable to provide an airlaid nonwoven comprising one or more sustainable polymer components. In contrast to polymers derived from petroleum sources, sustainable polymers are generally derived from a bio-based material. In some embodiments, a sustainable polymer component may also be considered biodegradeable. A special class of biodegradable product made with a bio-based material might be considered as compostable if it can be degraded in a composing environment. The European standard EN 13432, "Proof of Compostability of Plastic Products" may be used to determine if a fabric or film comprised of sustainable content could be classified as compostable.

In one such embodiment, the airlaid nonwoven comprises non-cellulose staple fibers comprising a sustainable polymer. In certain embodiments, the non-cellulose staple fibers are substantially free of synthetic materials, such as petroleum-based materials and polymers. For example, non-cellulose staple fibers comprising the airlaid nonwoven may have less than 25 weight percent of materials that are non-bio-based, and more preferably, less than 20 weight percent, less than 15 weight percent, less than 10 weight percent, and even more preferably, less than 5 weight percent of non-bio-based materials, based on the total weight of the airlaid nonwoven.

In one embodiment, sustainable polymers for use may include aliphatic polyester based polymers, such as polylactic acid (PLA) and polybutylene succinate (PBS), and bio-based derived polyethylene.

Aliphatic polyesters useful in the present invention may include homo- and copolymers of poly(hydroxyalkanoates), and homo- and copolymers of those aliphatic polyesters derived from the reaction product of one or more polyols with one or more polycarboxylic acids that are typically formed from the reaction product of one or more alkanediols with one or more alkanedicarboxylic acids (or acyl derivatives). Polyesters may further be derived from multifunctional polyols, e.g. glycerin, sorbitol, pentaerythritol, and combinations thereof, to form branched, star, and graft homo- and copolymers. Polyhydroxyalkanoates generally are formed from hydroxyacid monomeric units or derivatives thereof. These include, for example, polylactic acid, polyhydroxybutyrate, polyhydroxyvalerate, polycaprolactone and the like. Miscible and immiscible blends of aliphatic polyesters with one or more additional semicrystalline or amorphous polymers may also be used.

One useful class of aliphatic polyesters are poly(hydroxyalkanoates), derived by condensation or ring-opening polymerization of hydroxy acids, or derivatives thereof. Suitable poly(hydroxyalkanoates) may be represented by the formula: $H(O—R—C(O)—)_nOH$ where R is an alkylene moiety that may be linear or branched having 1 to 20 carbon atoms, preferably 1 to 12 carbon atoms optionally substituted by catenary (bonded to carbon atoms in a carbon chain) oxygen atoms; n is a number such that the ester is polymeric, and is preferably a number such that the molecular weight of the aliphatic polyester is at least 10,000, preferably at least 30,000, and most preferably at least 50,000 daltons. In certain embodiments, the molecular weight of the aliphatic polyester is typically less than 1,000,000, preferably less than 500,000, and most preferably less than 300,000 daltons. R may further comprise one or more caternary (i.e. in chain) ether oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e. polyglycolide). Copolymers of two or more of the above hydroxy acids may also be used, for example, poly(3-hydroxybutyrate-co-3-hydroxyvalerate), poly(lactate-co-3-hydroxypropanoate), poly(glycolide-co-p-dioxanone), and poly(lactic acid-co-glycolic acid). Blends of two or more of the poly(hydroxyalkanoates) may also be used, as well as blends with one or more semicrystalline or amorphous polymers and/or copolymers.

The aliphatic polyester may be a block copolymer of poly(lactic acid-co-glycolic acid). Aliphatic polyesters useful in the inventive compositions may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general formula:

$$HO(\overset{O}{\overset{\|}{C}}R''\overset{O}{\overset{\|}{C}})_n—[OR'O—\overset{O}{\overset{\|}{C}}—R''—\overset{O}{\overset{\|}{C}}—O]_m\cdot(R'O)_nH,$$

where R' and R" each represent an alkylene moiety that may be linear or branched having from 1 to 20 carbon atoms, preferably 1 to 12 carbon atoms, and m is a number such that the ester is polymeric, and is preferably a number such that the molecular weight of the aliphatic polyester is at least 10,000, preferably at least 30,000, and most preferably at least 50,000 daltons, but less than 1,000,000, preferably less than 500,000 and most preferably less than 300,000 daltons. Each n is independently 0 or 1. R' and R" may further comprise one or more caternary (i.e. in chain) ether oxygen atoms.

Examples of aliphatic polyesters include those homo- and copolymers derived from (a) one or more of the following diacids (or derivative thereof): succinic acid; adipic acid; 1,12 dicarboxydodecane; fumaric acid; glutartic acid; diglycolic acid; and maleic acid; and (b) one of more of the following diols: ethylene glycol; polyethylene glycol; 1,2-propane diol; 1,3-propanediol; 1,2-propanediol; 1,2-butanediol; 1,3-butanediol; 1,4-butanediol; 2,3-butanediol; 1,6-hexanediol; 1,2 alkane diols having 5 to 12 carbon atoms; diethylene glycol; polyethylene glycols having a molecular weight of 300 to 10,000 daltons, and preferably 400 to 8,000 daltons; propylene glycols having a molecular weight of 300 to 4000 daltons; block or random copolymers derived from ethylene oxide, propylene oxide, or butylene oxide; dipropylene glycol; and polypropylene glycol, and (c) optionally a small amount, i.e., 0.5-7.0 mole percent of a polyol with a functionality greater than two, such as glycerol, neopentyl glycol, and pentaerythritol.

Such polymers may include polybutylene succinate homopolymer, polybutylene adipate homopolymer, polybutyleneadipate-succinate copolymer, polyethylenesuccinate-adipate copolymer, polyethylene glycol succinate homopolymer and polyethylene adipate homopolymer.

Commercially available aliphatic polyesters include poly (lactide), poly(glycolide), poly(lactide-co-glycolide), poly (L-lactide-co-trimethylene carbonate), poly(dioxanone), poly(butylene succinate), and poly(butylene adipate).

The term "aliphatic polyester" covers—besides polyesters which are made from aliphatic and/or cycloaliphatic components exclusively also polyesters which contain besides aliphatic and/or cycloaliphatic units, aromatic units, as long as the polyester has substantial sustainable content.

In addition to PLA based resins, nonwoven fabrics in accordance with embodiments of the invention may include other polymers derived from an aliphatic component possessing one carboxylic acid group and one hydroxyl group, which are alternatively called polyhydroxyalkanoates (PHA). Examples thereof are polyhydroxybutyrate (PHB), poly-(hydroxybutyrate-co-hydroxyvaleterate) (PHBV), poly-(hydroxybutyrate-co-polyhydroxyhexanoate) (PHBH), polyglycolic acid (PGA), poly-(epsilon-caprolactione) (PCL) and preferably polylactic acid (PLA).

Examples of additional polymers that may be used in embodiments of the invention include polymers derived from a combination of an aliphatic component possessing two carboxylic acid groups with an aliphatic component possessing two hydroxyl groups, and are polyesters derived from aliphatic diols and from aliphatic dicarboxylic acids, such as polybutylene succinate (PBSU), polyethylene succinate (PESU), polybutylene adipate (PBA), polyethylene adipate (PEA), polytetramethy-lene adipate/terephthalate (PTMAT).

Useful aliphatic polyesters include those derived from semicrystalline polylactic acid. Poly(lactic acid) or polylactide (PLA) has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide) polymers may be obtained having different stereochemistries and different physical properties, including crystallinity. The L,L- or D,D-lactide yields semicrystalline poly (lactide), while the poly(lactide) derived from the D,L-lactide is amorphous.

Generally, polylactic acid based polymers are prepared from dextrose, a source of sugar, derived from field corn. In North America corn is used since it is the most economical source of plant starch for ultimate conversion to sugar. However, it should be recognized that dextrose can be derived from sources other than corn. Sugar is converted to lactic acid or a lactic acid derivative via fermentation through the use of microorganisms. Lactic acid may then be polymerized to form PLA. In addition to corn, other agriculturally-based sugar sources may be used including rice, sugar beets, sugar cane, wheat, cellulosic materials, such as xylose recovered from wood pulping, and the like.

The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, at least 90% of one isomer, or at least 95% of one isomer in order to maximize the crystallinity.

In some embodiments, an approximately equimolar blend of D-polylactide and L-polylactide is also useful. This blend forms a unique crystal structure having a higher melting point (about 210° C.) than does either the D-poly(lactide) and L-(polylactide) alone (about.190° C.), and has improved thermal stability.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid, alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-beta-methylvaleric acid, alpha-hydroxyoctanoic acid, alpha-hydroxydecanoic acid, alpha-hydroxymyristic acid, and alpha-hydroxystearic acid.

Blends of poly(lactic acid) and one or more other aliphatic polyesters, or one or more other polymers may also be used. Examples of useful blends include poly(lactic acid) and poly(vinyl alcohol), polyethylene glycol/polysuccinate, polyethylene oxide, polycaprolactone and polyglycolide.

In certain preferred embodiments, the aliphatic polyester component comprises a PLA based resin. A wide variety of different PLA resins may be used to prepare nonwoven fabrics in accordance with embodiments of the invention. The PLA resin should have proper molecular properties to be spun in spunbond processes. Examples of suitable include PLA resins are supplied from NatureWorks LLC, of Minnetonka, Minn. 55345 such as, grade 6752D, 6100D, and 6202D, which are believed to be produced as generally following the teaching of U.S. Pat. Nos. 5,525,706 and 6,807,973 both to Gruber et al. Other examples of suitable PLA resins may include L130, L175, and LX175, all from Corbion of Arkelsedijk 46, 4206 A C Gorinchem, the Netherlands.

In certain embodiments, the non-cellulose staple fibers have a sheath/core configuration in which the sheath and the core both comprise a PLA resin. In these embodiments, an airlaid nonwoven may be provided that is substantially free of synthetic polymer components, such as petroleum-based materials and polymers. For example, the non-cellulose staple fibers of the airlaid fabric may have a bicomponent arrangement in which the both components are PLA based to thus produce a staple fiber that is 100% PLA. As used herein, "100% PLA" may also include up to 5% additives including additives and/or masterbatches of additives to provide, by way of example only, color, softness, slip, antistatic protection, lubricity, hydrophilicity, liquid repellency, antioxidant protection and the like. In this regard, the non-cellulose staple fibers may comprise 95-100% PLA, such as from 96-100% PLA, 97-100% PLA, 98-100% PLA, 99-100% PLA, etc. When such additives are added as a masterbatch, for instance, the masterbatch carrier may primarily comprise PLA in order to facilitate processing and to maximize sustainable content within the fibers. For example, the non-cellulose staple fibers of the airlaid nonwoven may comprise one or more additional additives. In such embodiments, for instance, the additive may comprise at least one of a colorant, a softening agent, a slip agent, an antistatic agent, a lubricant, a hydrophilic agent, a liquid repellent, an antioxidant, and the like, or any combination thereof.

In one embodiment, the PLA polymer of the sheath may be the same PLA polymer as that of the core. In other embodiments, the PLA polymer of the sheath may be a different PLA polymer than that of the core. For example, the bicomponent staple fibers may comprise PLA/PLA bicomponent fibers such that the sheath comprises a first PLA grade, the core comprises a second PLA grade, and the first PLA grade and the second PLA grade are different (e.g., the first PLA grade has a lower melting point than the second PLA grade). By way of example only, the first PLA grade may comprise up to about 5% crystallinity, and the second PLA grade may comprise from about 40% to about 50% crystallinity.

In some embodiments, for instance, the first PLA grade may comprise a melting point from about 125° C. to about 135° C., and the second PLA grade may comprise a melting point from about 155° C. to about 170° C. In further embodiments, for example, the first PLA grade may comprise a weight percent of D isomer from about 4 wt. % to about 10 wt. %, and the second PLA grade may comprise a weight percent of D isomer of about 2 wt. %.

For example, in one embodiment, the core may comprise a PLA having a lower % D isomer of polylactic acid than that of the % D isomer PLA polymer used in the sheath. The PLA polymer with lower % D isomer will show higher degree of stress induced crystallization during spinning while the PLA polymer with higher D % isomer will retain a more amorphous state during spinning. The more amorphous sheath will promote bonding while the core showing a higher degree of crystallization will provide strength to the fiber and thus to the final bonded web. In one particular embodiment, the Nature Works PLA Grade PLA 6752 with 4% D Isomer can be used as the sheath while NatureWorks Grade 6202 with 2% D Isomer can be used as the core.

In some embodiments, the inventive airlaid nonwoven may comprise sustainable polymer components of biodegradable products that are derived from an aliphatic component possessing one carboxylic acid group (or a polyester forming derivative thereof, such as an ester group) and one hydroxyl group (or a polyester forming derivative thereof, such as an ether group) or may be derived from a combination of an aliphatic component possessing two carboxylic acid groups (or a polyester forming derivative thereof, such as an ester group) with an aliphatic component possessing two hydroxyl groups (or a polyester forming derivative thereof, such as an ether group).

Additional nonlimiting examples of bio-based polymers include polymers directly produced from organisms, such as polyhydroxyalkanoates (e.g., poly(beta-hydroxyalkanoate), poly(3-hydroxybutyrate-co-3-hydroxyvalerate, NODAX™), and bacterial cellulose; polymers extracted from plants and biomass, such as polysaccharides and derivatives thereof (e.g., gums, cellulose, cellulose esters, chitin, chitosan, starch, chemically modified starch), proteins (e.g., zein, whey, gluten, collagen), lipids, lignins, and natural rubber; and current polymers derived from naturally sourced monomers and derivatives, such as bio-polyethylene, bio-polypropylene, polytrimethylene terephthalate, polylactic acid, NYLON 11, alkyd resins, succinic acid-based polyesters, and bio-polyethylene terephthalate.

In some embodiments, the non-cellulose staple fibers may comprise a bio-based polymer comprising a bio-based polyethylene that is derived from a biological source. For example, bio-based polyethylene can be prepared from sugars that are fermented to produce ethanol, which in turn is dehydrated to provide ethylene. An example of a suitable sugar cane derived polyethylene is available from Braskem S.A. under the product name PE SHA7260.

In some embodiments of the non-cellulose staple fibers, the sheath may comprise a bio-based polyethylene, and the core may comprise a PLA polymer.

In some embodiments, the sheath may comprise a PLA or PBS polymer and the core a synthetic polymer, such as polypropylene.

In some embodiments, the non-cellulose staple fibers may include one or more additives that are blended with the polymer(s) during the melt extrusion phase. Examples of suitable additives include one or more of molecular and/or gas filters, such as zeolites, ion-exchange particles, activated carbon, and the like, colorants, such as pigments (e.g., $TiO_2$), UV stabilizers, hydrophobic agents, hydrophilic agents, antistatic agent, elastomers, compatibilizers antioxidants, anti-block agent, slip agent, optical brighteners, flame retardants, antimicrobials, such as copper oxide and zinc oxide and the like.

In some embodiments, the bamboo derived staple fibers may also be blended with staple fibers comprising conventional pulp fibers. In such applications, the content of the conventional wood pulp fibers may be up to 80% based on the total weight of the pulp fibers in the airlaid layer (e.g., total content of bamboo derived staple fibers and conventional pulp fibers).

Additional examples of conventional wood pulp fibers include pulps prepared from a variety of pulping processes, such a kraft pulp, sulfite pulp, thermo-mechanical pulp, etc. Conventional wood pulp fibers include treated and untreated pulps. Examples of conventional wood pulp fibers may include softwood fibers having an average fiber length of greater than 1 millimeter (mm) and particularly from about 2 mm to 5 mm. Such softwood fibers can include, but are not limited to: northern softwood, southern softwood, redwood, red cedar, hemlock, pine (e.g. southern pines), spruce (e.g. black spruce), combinations thereof, and so forth. Exemplary commercially available conventional wood pulp fibers suitable in the present invention include those available from Georgia Pacific under the designation 4722. Hardwood fibers, such as eucalyptus, maple, birch, aspen, and so forth, can also be used as conventional pulp fibers. In certain instances, secondary fibers obtained from recycled materials may be used, such as fiber pulp from sources such as, for example, newsprint, reclaimed paperboard and office waste.

In some embodiments, the airlaid nonwoven may include a super absorbent polymer or super absorbent fibers that are mixed with the bamboo derived staple fibers and non-cellulose fibers. When present, the superabsorbent may be in the form of fibers, particles, gels, etc. Generally speaking, superabsorbents are water-swellable materials capable of absorbing at least about 10 times their weight and, in some cases, at least about 30 times their weight, in an aqueous solution containing 0.9 weight percent sodium chloride. The superabsorbent may be formed from natural, synthetic and modified natural polymers and materials. Examples of synthetic superabsorbent polymers include the alkali metal and ammonium salts of poly(acrylic acid) and poly(methacrylic acid), poly(acrylamides), poly(vinyl ethers), maleic anhydride copolymers with ethers and alpha-olefins, poly(vinyl pyrrolidone), poly(vinylmorpholinone), poly(vinyl alcohol), and mixtures and copolymers thereof. Further superabsorbents include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Particularly suitable superabsorbent polymers are HYSORB 8800AD, available from BASF of Charlotte, N.C., and FAVOR SXM 9300, available from Degrussa Superabsorber of Greensboro, N.C. In addition, natural super absorbents may be used, such as Glucomannan. When present, the natural superabsorbent may comprise 100% of the superabsorbent, or may be blended with synthetic super absorbents.

In embodiments in which the airlaid layer includes multiple airlaid nonwoven layers, the super absorbent polymer or super absorbent fibers may be present in only one layer of the airlaid nonwoven or present in multiple airlaid layers of the airlaid nonwoven. When present, the super absorbent polymer or super absorbent fibers may be present in an amount from about 5 to 50 weight percent, and in particular, from about 10 to weight percent, based on the total weight of the airlaid nonwoven layer in which the super absorbent polymer or super absorbent fibers are present.

Certain embodiments of airlaid nonowovens in accordance with the invention are particularly useful in the production of composite sheet materials and laminates. In particular, airlaid nonowovens in accordance with one or more embodiments of the invention may be combined with one or more additional layers to provide composite sheet materials that are particularly useful in the manufacture of absorbent articles. Examples of additional layers that may be combined with the inventive airlaid nonowoven include nonwoven fabrics, such as spunbond, meltblown, spunlace, airlaid, and carded fabrics, and the like, tissue layers, such as a bamboo tissue layer, film layers, and the like, and combinations thereof.

In certain embodiments the inventive airlaid nonwoven is particularly useful as a component in an acquisition/distribution layer or as an absorbent core in an absorbent article.

II. Fluid Transfer Layer of an Absorbent Article

In certain embodiments, airlaid nonwovens in accordance with embodiments of the present invention are particularly useful as a fluid transfer layer in an absorbent article. Advantageously, the transfer layer helps to provide controlled transfer of the fluid from a topsheet to the core. In particular, the transfer layer helps to provide temporarily storage capacity of the fluid prior to transfer to the core.

In certain embodiments, the transfer layer comprises an acquisition/distribution layer (AQDL) component in the manufacture of absorbent articles. The fluid AQDL component generally comprises a composite sheet material comprising the inventive airlaid nonwoven in combination with one or more additional layers, such as a carded nonwoven layer. In some embodiments, the additional layer may be selected from the group consisting of nonwovens, such as spunbond, spunlace, meltblown, and carded nonwovens, films, and cellulosic tissue papers.

Figure 3:
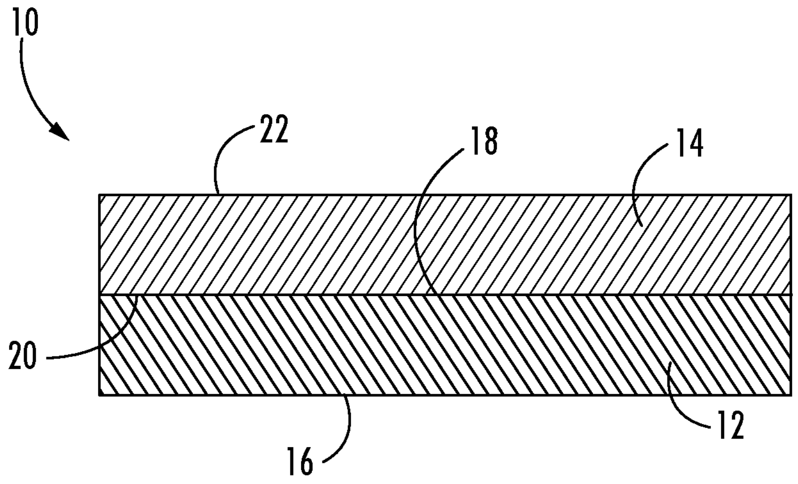
FIG. 3 is a composite sheet in accordance with at least one embodiment of the present invention.

With reference to FIG. 3, a composite sheet material in accordance with at least one embodiment of the invention is shown and designated by reference character 10. In the illustrated embodiment, the sheet material 10 comprises a fluid acquisition component 12 and an airlaid component 14 overlying the fluid acquisition component. The airlaid component 14 is in accordance with at least one embodiment of the invention and comprises a blend of non-cellulose staple fibers and bamboo derived staple fibers. Examples of non-cellulose staple fiber and bamboo derived staple fibers are discussed above in connection with the inventive airlaid nonwoven.

In certain embodiments, the fluid acquisition component includes at least one nonwoven layer having a first outer surface 16 and a second outer surface 18. Similarly, the airlaid component includes a first outer surface 20 and a second outer surface 22.

In one embodiment, the outer surface 18 of the fluid acquisition is component 12 is disposed adjacent and opposite outer surface 20 of the airlaid component 14. In preferred embodiments, the opposing outer surfaces 18, 20 of the fluid distribution and airlaid nonwoven components 12, 14 are disposed directly opposite each other so that the surfaces of each component are in contact with each other.

Figure 4:
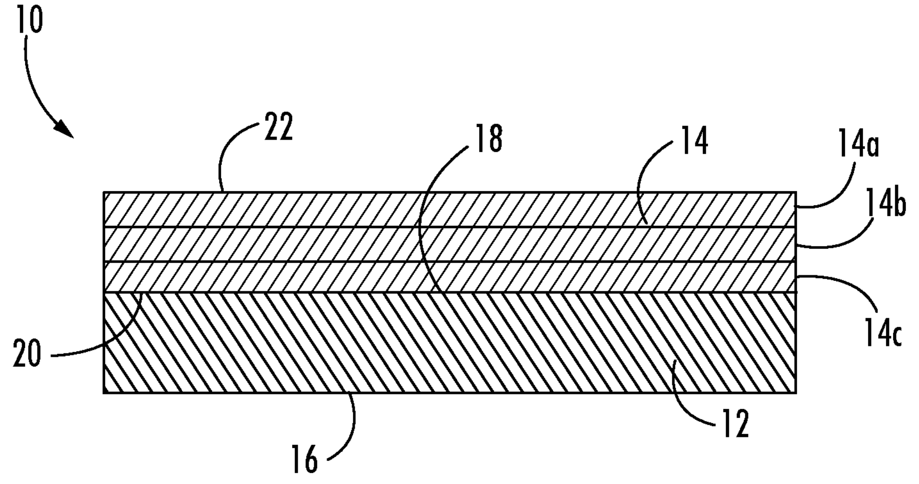
FIG. 4 is a cross-sectional side view of a composite sheet in accordance with at least one embodiment of the present invention in which the composite sheet includes a plurality of airlaid layers.

In some embodiments, the airlaid nonwoven component 14 may comprise one or more airlaid layers. In this regard, FIG. 4 illustrates an embodiment of the invention in which the airlaid component comprises a plurality of airlaid layers that are formed overlying the fluid acquisition component 12. Preferably, each of the airlaid layers are adjacent to, and in direct contact with, immediately adjacent layers of the airlaid component so that adjacent layers are in fluid communication with respect to each other.

In some embodiments, the non-cellulose staple fibers of the airlaid component and at least some of the fibers of the fluid acquisition component both comprise compatible polymers to help facilitate bonding of fibers in the two components to each other.

Typically, a fluid AQDL component need to balance properties in order to quickly move fluids away from the skin of the wearer, and uniformly distribute them into the absorbent core of the absorbent article. If the fluid is transported too quickly through the AQDL component, the fluid may not distribute laterally (in the x-y directions) through the layer. This may result in too much fluid being localized in one region of the absorbent core. Ideally, it is desirable to have the fluid move quickly through the fluid AQDL component while at the same time, the fluid is distributed laterally through the component. This allows the fluid to be absorbed over a large surface area of the absorbent core.

To achieve this desired balance, it is important that the fluid AQDL component have good fluid transport properties, good wicking properties (capillary action of the fluid moving through the component), low fluid acquisition times (the length of time it takes for a material to absorb a given amount of fluid) as well as good fluid retention properties. The first three properties contribute to how quickly the fluid is moved away from the skin of the wearer and into the absorbent core, and the fluid retention property helps to balance these properties to allow the fluid to be laterally distributed prior to transport into the absorbent core.

As absorbent articles, such as femcare products, diapers, and incontinence products, are typically meant to worn by an individual, the comfort of the material to the wearer is also important. If the material is inflexible, stiff, or rigid, the wearer is most likely to reject the absorbent article. Accordingly, it is desirable for the absorbent article to not only provide the balance of the above-described properties, but to also to have resiliency so to provide improved comfort and fit to the wearer.

The inventors of the present invention have found that composite sheets in accordance with the invention provide a good balance of fluid absorption, fluid wicking, fluid acquisition time, and fluid retention, as well as providing a composite sheet having good flexibility, resiliency, and reduced thickness. As a result, composite sheet materials in accordance with embodiments of the invention are particularly useful as a fluid AQDL component in the manufacture of absorbent articles.

In particular, composite sheet materials comprising the inventive airlaid nonwoven exhibit decreases in thickness, improved wicking capabilities and increased flexibility in comparison to a similar composite sheet comprising an airlaid nonwoven having staple fibers comprising conventional wood pulp fibers in lieu of bamboo derived staple fibers.

Surprisingly, composite sheets in accordance with embodiments of the invention exhibit reduced thickness in comparison to a similar composite sheet having fibers comprising conventional wood pulp fibers without significantly sacrificing the fluid retention properties of the composite sheet. Typically, one would expect, for a given basis weight, that a reduction in thickness of the AQDL component would also result in a reduction in fluid retention because the void spaces between fibers would be reduced. In contrast to this expectation, the inventors have discovered that the use of bamboo derived staple fibers in lieu of fibers comprising conventional wood pulp fibers provided decreases in thickness ranging from 10 to 75% without significantly sacrificing the fluid retention properties of the AQDL component.

In certain embodiments, composite sheet materials (i.e., including at least one airlaid nonwoven comprising bamboo derived staple fibers) in accordance with embodiments of the invention exhibit a decrease in thickness (caliper) ranging from 10 to 60%, and in particular, from about 20 to 50%, and more particularly, from 25 to 45% in comparison to a similar composite sheet in which the airlaid nonwoven component comprises staple fibers comprising conventional wood pulp fibers in lieu of bamboo derived staple fibers.

In some embodiments, the composite sheet material may exhibit a thickness less than any one of 2.0 mm, 1.95 mm, 1.90 mmm 1.85 mm, 1.80 mm, 1.75 mm, 1.70 mm, 1.65 mm, 1.60 mm, 1.55 mm, 1.50 mm, 1.45 mm, 1.40 mm, 1.35 mm, 1.30 mm, 1.25 mm, 1.20 mm, 1.15 mm, 1.10 mm, and 1.05 mm. In certain embodiments, the composite sheet material has a thickness ranging from about 1.0 to 2.0 mm, 1.1 to 1.9 mm, 1.2 to 1.3 mm, and 1.25 to 1.40 mm.

In certain embodiments, composite sheet materials in accordance with embodiments of the invention exhibit a decrease in MD stiffness ranging from 10 to 50%, and in particular, from about 15 to 35%, and more particularly, from 20 to 30% in comparison to a similar composite sheet material in which the airlaid nonwoven component comprises staple fibers comprising conventional wood pulp fibers in lieu of bamboo derived staple fibers.

In one embodiment, composite sheet materials in accordance with one or more embodiments of the invention may exhibit a MD stiffness less than 46 mN/cm, less than 44, less than 42, less than 40, less than 38, less than 36, less than 34, less than 32, less than 30, less than 28, less than 26, less than 24, less than 22, and and less than 20 mN/cm. In some embodiments, composite sheet materials may exhibit a MD stiffness ranging from about 20 to 50 mN/cm, such as from about 25 to 40 mN/cm, and 28 to 36 mN/cm. In one particular embodiment, the composite sheet material may exhibit a MD stiffness ranging from 25 to 40 mN/cm.

In certain embodiments, composite sheet materials in accordance with embodiments of the invention exhibit a decrease in CD stiffness ranging from 10 to 60%, and in particular, from about 20 to 50%, and more particularly, from 25 to 45% in comparison to a similar composite sheet material in which the airlaid nonwoven comprises staple fibers comprising conventional wood pulp fibers in lieu of bamboo derived staple fibers.

In one embodiment, composite sheet materials in accordance with one or more embodiments of the invention may exhibit a CD stiffness less than 15 mN/cm, less than 14, less than 13, less than 12, less than 11, less than 10, less than 9, less than 8, less than 7, less than 6, and less than 5 mN/cm. In some embodiments, composite sheet materials may exhibit a CD stiffness ranging from about 5 to 15 mN/cm, such as from about 6 to 14 mN/cm, 7 to 12 mN/cm, or 8 to 11 mN/cm.

Advantageously, a reduction in stiffness of the composite sheet material helps to provide a reduction in the overall stiffness in the absorbent article comprising the composite sheet material, which results in an increased flexibility in the absorbent article. Reductions in thickness and increases in flexibility are generally desirable because the help to improve the comfort and wearability of the absorbent article as well as providing an article having improved discreetness.

Further, it has been observed that composite sheet materials in accordance with certain embodiments of the invention exhibit improved flexibility (e.g., reduced stiffness) in comparison to a similar composite sheet material in which the airlaid nonwoven component comprises staple fibers comprising conventional wood pulp fibers in lieu of bamboo derived staple fibers.

Advantageously, these improvements associated with the use of bamboo derived staple fibers are provided without significantly sacrificing other desirable fluid management properties of the composite sheet material, such as fluid acquisition time, fluid retention, fluid absorption, and fluid capacity.

In addition, composite sheet materials in accordance with certain embodiments of the invention exhibit improved wicking properties (capillary action of the fluid moving through the component) in comparison to a similar composite sheet material in which the airlaid nonwoven component comprises staple fibers of conventional wood pulp fibers in lieu of bamboo derived staple fibers.

In certain embodiments, composite sheet materials in accordance with embodiments of the invention exhibit an increase in vertical wicking height ranging from 50 to 150%, and in particular, from about 75 to 140%, and more particularly, from 90 to 130% in comparison to a similar composite sheet materials in which the airlaid nonwoven component comprises staple fibers comprising conventional wood pulp fibers in lieu of bamboo derived staple fibers.

In certain embodiments, composite sheet materials in accordance with embodiments of the invention exhibit an increase in wicking rate ranging from 40 to 120%, and in particular, from about 50 to 110%, and more particularly, from 60 to 100% in comparison to a similar composite sheet material in which the airlaid nonwoven component comprises staple fibers comprising conventional wood pulp fibers in lieu of bamboo derived staple fibers. In some embodiments, composite sheet materials in accordance with embodiments of the invention exhibit an increase in wicking rate ranging from 75 to 95%, in comparison to a composite sheet material in which the airlaid nonwoven component comprises staple fibers comprising conventional wood pulp fibers in lieu of bamboo derived staple fibers.

In one embodiment, composite sheet materials in accordance with embodiments of the invention exhibit a wicking rate of at least 30 mm/15 sec., at least 32, at least 34, at least 36, at least 38, at least 40, at least 42, at least 44, and at least 46 mm/15 sec. In some embodiments, composite sheet materials in accordance with embodiments of the invention exhibit a wicking rate from about 30 to 50 mm/15 sec, such as from about 32 to 40 mm/15 sec, or 34 to 38 mm/15 sec.

In one embodiment, composite sheet materials in accordance with embodiments of the invention exhibit a vertical wicking height of at least 30 mm, at least 32, at least 34, at least 36, at least 38, at least 40, at least 42, at least 44, at least 46, at least 48, at least 50, at least 52, at least 54, at least 56, at least 58, at least 60, at least 62, at least 64, at least 66, at least 68, or at least 70 mm. In some embodiments, composite sheet materials in accordance with embodiments of the invention exhibit a vertical wicking height from about 30 to 70 mm, such as from about 35 to 65 mm, or 40 to 60 mm.

In one aspect, composite sheets in accordance with certain embodiments of the invention are characterized by a thickness ranging from about 1.0 to 2.0 mm, a CD stiffness ranging from about 5 to 15 mN/cm and a MD stiffness ranging from about 20 to 50 mN/cm. In a further aspect, the composite sheet may also be characterized by a wicking rate from about 30 to 50 mm/15 sec, and a vertical wicking height from about 30 to 70 mm.

In one aspect, composite sheets in accordance with certain embodiments of the invention are characterized by a thickness ranging from about 1.25 to 1.40 mm, a CD stiffness ranging from about 6 to 14 mN/cm and a MD stiffness ranging from about 25 to 40 mN/cm. In a further aspect, the composite sheet may also be characterized by a wicking rate from about 32 to 40 mm/15 sec, and a vertical wicking height from about 35 to 65 mm.

In one aspect, composite sheets in accordance with certain embodiments of the invention are characterized by fluid acquisition times ranging from about 0.75 seconds to about 2 seconds, and in particular, from about 0.8 to 1.5 seconds, and in particular, from about 0.84 to 1.3 seconds.

In one aspect, composite sheets in accordance with certain embodiments of the invention are characterized by a fluid absorption ranging from about 15 to 30 g/g, and in particular, from about 20 to 26 g/g, and in particular, from about 20 to 25 g/g.

In one aspect, composite sheets in accordance with certain embodiments of the invention are characterized by a fluid retention ranging from about 8 to 15 g/g, and in particular, from about 9 to 14 g/g, and in particular, from about 10 to 12 g/g.

In one aspect, composite sheets in accordance with certain embodiments of the invention are characterized by a vertical fluid wicking height ranging from about 10 to 50 mm, and in particular, from about 15 to 45 mm, and more particularly, from about 15 to 40 mm.

In one aspect, composite sheets in accordance with certain embodiment of the invention are characterized by a resiliency ranging from about 30 to 60%, and in particular, from about 35 to 55%, and more particularly, from about 40 to 50%.

In one embodiment, composite sheets in accordance with the invention may be characterized by a fluid acquisition time ranging from about 0.5 seconds to about 2 seconds; a fluid absorption ranging from about 15 to 30 g/g; a fluid retention ranging from about 8 to 15 g/g; a fluid wicking height ranging from about 10 to 50 mm; and a resiliency ranging from about 30 to 60%. For example, the composite sheet may have a fluid acquisition time ranging from about 0.65 to 1.5 seconds; a fluid absorption ranging from about 20 to 26 g/g; a fluid retention ranging from about 9 to 14 g/g; a fluid wicking height ranging from about 15 to 45 mm; and a resiliency ranging from about 35 to 55%. In certain embodiments, the composite sheet may have a fluid acquisition time ranging from about 0.84 to 1.3 seconds; a fluid absorption ranging from about 20 to 25 g/g; a fluid retention ranging from about 10 to 12 g/g; a fluid wicking height ranging from about 15 to 40 mm; and a resiliency ranging from about 40 to 55%.

In a preferred embodiment, the composite sheet has a fluid acquisition of about 1.25 seconds; a fluid absorption of about 25 g/g; a fluid retention of about 10 g/g; a vertical fluid wicking height of about 40 mm; and a resiliency of about 40%.

The basis weight of the composite sheet may range from about 25 to 400 grams per square meter ($g/m^2$), and in particular, from about 40 to 225 $g/m^2$ and 50 to 250 $g/m^2$ and more particularly, from about 50 to 180 $g/m^2$. In a preferred embodiment, the composite sheet has a basis weight that is about 50 to 100 $g/m^2$.

The thickness of the composite sheet may range from about 0.7 to 6 mm, and in particular, from about 1.3 to 4.5 mm, and more particularly, from about 1.5 to 3.0 mm. In a preferred embodiment, the composite sheet has a thickness that is about 1.6 to 2.5 mm. In a preferred embodiment, the thickness of the composite sheet is from about 1.0 to 1.5, and in particular, from about 1.2 to 1.4 mm.

In general, the mass of the fluid acquisition component comprises from about 8 to 85 weight percent of the composite sheet, based on the total weight of the composite sheet. In one embodiment, the mass of the fluid acquisition component comprises from about 20 to 75 weight percent of the composite sheet, and in particular, from about 30 to 60 weight percent, based on the total weight of the composite sheet.

The mass of the airlaid component comprises from about 15 to 92 weight percent of the composite sheet, based on the total weight of the composite sheet. In one embodiment, the mass of the airlaid component comprises from about 20 to 80 weight percent of the composite sheet, and in particular, from about 30 to 70 weight percent, based on the total weight of the composite sheet.

Fluid Acquisition Component

In one embodiment, the fluid acquisition component comprises a fluid acquisition layer comprising a nonwoven fabric having a relatively permeable and porous structure so that a fluid, upon impinging on the surface of the fluid acquisition layer, is quickly transported through the fluid acquisition layer, and into the airlaid component 14. The permeable and porous nature of the fluid acquisition layer may generally be characterized by the density of the layer. For example, the density of the fluid acquisition layer may be from about 0.02 to 0.07 $g/cm^3$, and in particular, from about 0.03 to 0.06 $g/cm^3$. In a preferred embodiment, the density of the fluid acquisition layer is from about 0.04 to 0.05 $g/cm^3$.

A wide variety of different nonwoven fabrics may be used as the fluid acquisition layer. In one embodiment, the nonwoven fabric of the fluid acquisition layer comprises a carded nonwoven fabric comprising staple fibers. Typical lengths of the staple fibers in the fluid acquisition layer may range from about 20 to 100 mm, and in particular, from about 25 to 60 mm, and more particularly, from about 35 to 55 mm.

Other examples of nonwovens that may be used as the fluid acquisition layer may include latex bonded carded fabrics and spunlace nonwovens. The fibers of the fluid acquisition layer may be bonded in a variety of manners including, thermal bonding, resin bonding, stitch bonding, mechanical bonding, such as needle punch or hydroentanglement, and the like. In a preferred embodiment, the fibers of the fluid acquisition layer are bonded via air through thermal bonding.

In some embodiments, the fibers of the fluid acquisition layer may be bonded via thermal calender bonding. In certain other embodiments, the fibers of the fluid acquisition layer are not subjected to thermal calender bonding. In certain embodiments, the fibers of the fluid acquisition layer are not bonded via hydraulic entanglement and are characterized by the absence of a hydraulic entanglement process in the bonding of the fibers.

Suitable materials for the staple fibers for use in the fluid acquisition component may comprise monocomponent or multicomponent fibers, or mixtures of moncomponent and multicomponent fibers. In a preferred embodiment, the staple fibers of the fluid acquisition component comprise bicomponent fibers having a sheath/core configuration.

In one embodiment, the staple fibers of the fluid acquisition component comprise bicomponent fibers have a sheath/core configuration. Examples of bicomponent fibers include side-by-side, islands in the sea, and sheath/core arrangements. Preferably, the fibers have a sheath/core structure in which the sheath comprises a first polymer component, and the core comprises a second polymer component. In this arrangement, the polymers of the first and second polymer components may be the same or different from each other. For example, in one embodiment, the sheath comprises a first polymer component, and the core comprises a second polymer component that is different or the same as the first polymer component. In a preferred embodiment, the first and second polymer components of the bicomponent fibers are different from each other.

In some embodiments the staple fibers of the fluid acquisition component may have a sheath/core configuration in which the core is centered relative to the sheath. Alternatively, the core may be present in an off-set configuration relative to the sheath. In this configuration, the core not centrally aligned relative to the sheath. As a result, when heat is applied, such as during bonding, the fibers will have a tendency to curl or crimp, which in turn may help provide loft to the fluid acquisition component.

In one embodiment, the first polymer component of the sheath comprises a polymer having a lower melting temperature than that of the second polymer component comprising the core. The lower melting polymer of the sheath will promote bonding while the polymer component of the core having a higher melting temperature will provide strength to the fiber and thus to the final bonded nonwoven.

Generally, the weight percentage of the sheath to that of the core in the fibers may vary widely depending upon the desired properties of the nonwoven fabric. For example, the weight ratio of the sheath to the core may vary between about 10:90 to 90:10, and in particular from about 20:80 to 80:20. In a preferred embodiment, the weight ratio of the sheath to the core is about 60:40 to 40:60, with a weight ratio of about 50:50 being preferred.

A wide variety of polymers may be used for preparing staple fibers for use in the fluid acquisition component. Examples of suitable fibers include may include polyolefins, such as polypropylene and polyethylene, and copolymers thereof, polyesters, such as polyethylene terephthalate (PET), polytrimethylene terephthalate (PTT), and polybutylene terephthalate (PBT), nylons, polystyrenes, copolymers, and blends thereof, and other synthetic polymers that may be used in the preparation of fibers. In one embodiment, the staple fibers have a sheath/core configuration comprising a polyethylene sheath and a polypropylene core. In other embodiments, the staple fibers may have a sheath/core configuration comprising a polyethylene sheath and a polyester core, such as a core comprising polyethylene terephthalate.

In some embodiments, the staple fibers of the fluid acquisition component may comprise a blend of fibers such as a blend of bicomponent staple fibers having a polyethylene sheath and a polyethylene terephthalate core, and bicomponent staple fibers having a polyethylene sheath and a polypropylene core. In one embodiment, the fibers of the fluid acquisition component may include eccentric bicomponent staple fibers having a polyethylene sheath and a polyethylene terephthalate core, a fineness of 4.3 dtex, and an average length of 38 to 51 mm. Examples of such fibers are available from Indorama Polyester Industries Public Company Limited under the product name TS47.

In one embodiment, the staple fibers of the fluid acquisition component may comprise bicomponent staple fibers having a polyethylene sheath and a polyethylene terephthalate core. One such example is bicomponent staple fiber having a fineness of 2.2 dtex, and an average length of 3 mm, which are available from Toray Chemical Korea Inc. under the product name EZBON A (UN-204). A further example is an eccentric bicomponent staple fibers having a polyethylene sheath and a polyethylene terephthalate core. Such a fiber is available from Indorama Polyester Industries Public Company Limited under the product name TS47 (a fineness of 4.3 dtex, and an average length of 3 mm). Another example is a bicomponent staple fibers having a polyethylene sheath and a polyethylene terephthalate core is available from Trevira under the product designation T255 staple fibers. These staple fibers have a fineness of 4.3 dtex, and an average length of 3 mm.

In another embodiment, the staple fibers of the fluid acquisition component may comprise bicomponent staple fibers having a polyethylene sheath and a polypropylene core. One such example is a staple fiber having a fineness of 4.0 dtex, and an average length of 40 mm, which are available from Yangzhou Petrochemical Co. Ltd. under the product name Y116. Another example of bicomponent staple fibers having a polyethylene sheath and a polypropylene core, a denier of 6.0, and an average length of 51 mm, are available from JiangNan High Polymer Fiber under the product designation JNGX-PZ11-6*51L.

In some embodiments, the fluid acquisition component staple fibers may comprise blends of fibers, such as blends comprising bicomponent PE/PET and PE/PP staple fibers.

The above noted polymers are generally considered to be derived from synthetic sources, such as a petroleum derived polymer. In some embodiments, it may be desirable to provide a fluid acquisition component comprising one or more sustainable polymer components. In contrast to polymers derived from petroleum sources, sustainable polymers are generally derived from a bio-based material. In some embodiments, a sustainable polymer component may also be considered biodegradeable. A special class of biodegradable product made with a bio-based material might be considered as compostable if it can be degraded in a composing environment. The European standard EN 13432, "Proof of Compostability of Plastic Products" may be used to determine if a fabric or film comprised of sustainable content could be classified as compostable.

In one such embodiment, the fluid acquisition component comprises staple fibers comprising a sustainable polymer. In certain embodiments, the fluid acquisition component staple fibers are substantially free of synthetic materials, such as petroleum-based materials and polymers. For example, staple fibers comprising the fluid acquisition component may have less than 25 weight percent of materials that are non-bio-based, and more preferably, less than 20 weight percent, less than 15 weight percent, less than 10 weight percent, and even more preferably, less than 5 weight percent of non-bio-based materials, based on the total weight of the airlaid nonwoven.

In one embodiment, sustainable polymers for use may include aliphatic polyester based polymers, such as polylactic acid (PLA) and polybutylene succinate (PBS), bio-based derived polyethylene, bio-based derived polypropylene, bio-based derived polyesters, such as bio-based derived polyethylene terephthalate (PET), and the like, and combinations thereof.

Aliphatic polyesters useful in the present invention may include homo- and copolymers of poly(hydroxyalkanoates), and homo- and copolymers of those aliphatic polyesters derived from the reaction product of one or more polyols with one or more polycarboxylic acids that are typically formed from the reaction product of one or more alkanediols with one or more alkanedicarboxylic acids (or acyl derivatives). Polyesters may further be derived from multifunctional polyols, e.g. glycerin, sorbitol, pentaerythritol, and combinations thereof, to form branched, star, and graft homo- and copolymers. Polyhydroxyalkanoates generally are formed from hydroxyacid monomeric units or derivatives thereof. These include, for example, polylactic acid, polyhydroxybutyrate, polyhydroxyvalerate, polycaprolactone and the like. Miscible and immiscible blends of aliphatic polyesters with one or more additional semicrystalline or amorphous polymers may also be used.

One useful class of aliphatic polyesters are poly(hydroxyalkanoates), derived by condensation or ring-opening polymerization of hydroxy acids, or derivatives thereof. Suitable poly(hydroxyalkanoates) may be represented by the formula: $H(O—R—C(O)—)_nOH$ where R is an alkylene moiety that may be linear or branched having 1 to 20 carbon atoms, preferably 1 to 12 carbon atoms optionally substituted by catenary (bonded to carbon atoms in a carbon chain) oxygen atoms; n is a number such that the ester is polymeric, and is preferably a number such that the molecular weight of the aliphatic polyester is at least 10,000, preferably at least 30,000, and most preferably at least 50,000 daltons. In certain embodiments, the molecular weight of the aliphatic polyester is typically less than 1,000,000, preferably less than 500,000, and most preferably less than 300,000 daltons. R may further comprise one or more caternary (i.e. in chain) ether oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e. polyglycolide). Copolymers of two or more of the above hydroxy acids may also be used, for example, poly(3-hydroxybutyrate-co-3-hydroxyvalerate), poly(lactate-co-3-hydroxypropanoate), poly(glycolide-co-p-dioxanone), and poly(lactic acid-co-glycolic acid). Blends of two or more of the poly(hydroxyalkanoates) may also be used, as well as blends with one or more semicrystalline or amorphous polymers and/or copolymers.

The aliphatic polyester may be a block copolymer of poly(lactic acid-co-glycolic acid). Aliphatic polyesters useful in the inventive compositions may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general formula:

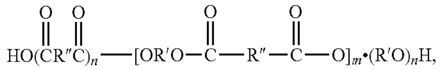

where R' and R" each represent an alkylene moiety that may be linear or branched having from 1 to 20 carbon atoms, preferably 1 to 12 carbon atoms, and m is a number such that the ester is polymeric, and is preferably a number such that the molecular weight of the aliphatic polyester is at least 10,000, preferably at least 30,000, and most preferably at least 50,000 daltons, but less than 1,000,000, preferably less than 500,000 and most preferably less than 300,000 daltons. Each n is independently 0 or 1. R' and R" may further comprise one or more caternary (i.e. in chain) ether oxygen atoms.

Examples of aliphatic polyesters include those homo- and copolymers derived from (a) one or more of the following diacids (or derivative thereof): succinic acid; adipic acid; 1,12 dicarboxydodecane; fumaric acid; glutartic acid; diglycolic acid; and maleic acid; and (b) one of more of the following diols: ethylene glycol; polyethylene glycol; 1,2-propane diol; 1,3-propanediol; 1,2-propanediol; 1,2-butanediol; 1,3-butanediol; 1,4-butanediol; 2,3-butanediol; 1,6-hexanediol; 1,2 alkane diols having 5 to 12 carbon atoms; diethylene glycol; polyethylene glycols having a molecular weight of 300 to 10,000 daltons, and preferably 400 to 8,000 daltons; propylene glycols having a molecular weight of 300 to 4000 daltons; block or random copolymers derived from ethylene oxide, propylene oxide, or butylene oxide; dipropylene glycol; and polypropylene glycol, and (c) optionally a small amount, i.e., 0.5-7.0 mole percent of a polyol with a functionality greater than two, such as glycerol, neopentyl glycol, and pentaerythritol.

Such polymers may include polybutylene succinate homopolymer, polybutylene adipate homopolymer, polybutyleneadipate-succinate copolymer, polyethylenesuccinate-adipate copolymer, polyethylene glycol succinate homopolymer and polyethylene adipate homopolymer.

Commercially available aliphatic polyesters include poly (lactide), poly(glycolide), poly(lactide-co-glycolide), poly (L-lactide-co-trimethylene carbonate), poly(dioxanone), poly(butylene succinate), and poly(butylene adipate).

The term "aliphatic polyester" covers—besides polyesters which are made from aliphatic and/or cycloaliphatic components exclusively also polyesters which contain besides aliphatic and/or cycloaliphatic units, aromatic units, as long as the polyester has substantial sustainable content.

In addition to PLA based resins, nonwoven fabrics in accordance with embodiments of the invention may include other polymers derived from an aliphatic component possessing one carboxylic acid group and one hydroxyl group, which are alternatively called polyhydroxyalkanoates (PHA). Examples thereof are polyhydroxybutyrate (PHB), poly-(hydroxybutyrate-co-hydroxyvaleterate) (PHBV), poly-(hydroxybutyrate-co-polyhydroxyhexanoate) (PHBH), polyglycolic acid (PGA), poly-(epsilon-caprolactione) (PCL) and preferably polylactic acid (PLA).

Examples of additional polymers that may be used in embodiments of the invention include polymers derived from a combination of an aliphatic component possessing two carboxylic acid groups with an aliphatic component possessing two hydroxyl groups, and are polyesters derived from aliphatic diols and from aliphatic dicarboxylic acids, such as polybutylene succinate (PBSU), polyethylene succinate (PESU), polybutylene adipate (PBA), polyethylene adipate (PEA), polytetramethy-lene adipate/terephthalate (PTMAT).

Useful aliphatic polyesters include those derived from semicrystalline polylactic acid. Poly(lactic acid) or polylactide (PLA) has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide) polymers may be obtained having different stereochemistries and different physical properties, including crystallinity. The L,L- or D,D-lactide yields semicrystalline poly (lactide), while the poly(lactide) derived from the D,L-lactide is amorphous.

Generally, polylactic acid based polymers are prepared from dextrose, a source of sugar, derived from field corn. In North America corn is used since it is the most economical source of plant starch for ultimate conversion to sugar. However, it should be recognized that dextrose can be derived from sources other than corn. Sugar is converted to lactic acid or a lactic acid derivative via fermentation through the use of microorganisms. Lactic acid may then be polymerized to form PLA. In addition to corn, other agriculturally-based sugar sources may be used including rice, sugar beets, sugar cane, wheat, cellulosic materials, such as xylose recovered from wood pulping, and the like.

The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, at least 90% of one isomer, or at least 95% of one isomer in order to maximize the crystallinity.

In some embodiments, an approximately equimolar blend of D-polylactide and L-polylactide is also useful. This blend forms a unique crystal structure having a higher melting point (about 210° C.) than does either the D-poly(lactide) and L-(polylactide) alone (about.190° C.), and has improved thermal stability.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid, alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-beta-methylvaleric acid, alpha-hydroxyoctanoic acid, alpha-hydroxydecanoic acid, alpha-hydroxymyristic acid, and alpha-hydroxystearic acid.

Blends of poly(lactic acid) and one or more other aliphatic polyesters, or one or more other polymers may also be used. Examples of useful blends include poly(lactic acid) and poly(vinyl alcohol), polyethylene glycol/polysuccinate, polyethylene oxide, polycaprolactone and polyglycolide.

In certain preferred embodiments, the aliphatic polyester component comprises a PLA based resin. A wide variety of different PLA resins may be used to prepare nonwoven fabrics in accordance with embodiments of the invention. The PLA resin should have proper molecular properties to be spun in spunbond processes. Examples of suitable include PLA resins are supplied from NatureWorks LLC, of Minnetonka, Minn. 55345 such as, grade 6752D, 6100D, and 6202D, which are believed to be produced as generally following the teaching of U.S. Pat. Nos. 5,525,706 and 6,807,973 both to Gruber et al. Other examples of suitable PLA resins may include L130, L175, and LX175, all from Corbion of Arkelsedijk 46, 4206 A C Gorinchem, the Netherlands.

In certain embodiments, the staple fibers of the fluid acquisition component have a sheath/core configuration in which the sheath and the core both comprise a PLA resin. In these embodiments, an airlaid nonwoven may be provided that is substantially free of synthetic polymer components, such as petroleum-based materials and polymers. For example, the staple fibers of the fluid acquisition component may have a bicomponent arrangement in which the both components are PLA based to thus produce a staple fiber that is 100% PLA. As used herein, "100% PLA" may also include up to 5% additives including additives and/or masterbatches of additives to provide, by way of example only, color, softness, slip, antistatic protection, lubricity, hydrophilicity, liquid repellency, antioxidant protection and the like. In this regard, the fluid acquisition component staple fibers may comprise 95-100% PLA, such as from 96-100% PLA, 97-100% PLA, 98-100% PLA, 99-100% PLA, etc. When such additives are added as a masterbatch, for instance, the masterbatch carrier may primarily comprise PLA in order to facilitate processing and to maximize sustainable content within the fibers. For example, the staple fibers of the fluid acquisition component may comprise one or more additional additives. In such embodiments, for instance, the additive may comprise at least one of a colorant, a softening agent, a slip agent, an antistatic agent, a lubricant, a hydrophilic agent, a liquid repellent, an antioxidant, and the like, or any combination thereof.

In one embodiment, the PLA polymer of the sheath may be the same PLA polymer as that of the core. In other embodiments, the PLA polymer of the sheath may be a different PLA polymer than that of the core. For example, the bicomponent staple fibers may comprise PLA/PLA bicomponent fibers such that the sheath comprises a first PLA grade, the core comprises a second PLA grade, and the first PLA grade and the second PLA grade are different (e.g., the first PLA grade has a lower melting point than the second PLA grade). By way of example only, the first PLA grade may comprise up to about 5% crystallinity, and the second PLA grade may comprise from about 40% to about 50% crystallinity.

In some embodiments, for instance, the first PLA grade may comprise a melting point from about 125° C. to about 135° C., and the second PLA grade may comprise a melting point from about 155° C. to about 170° C. In further embodiments, for example, the first PLA grade may comprise a weight percent of D isomer from about 4 wt. % to about 10 wt. %, and the second PLA grade may comprise a weight percent of D isomer of about 2 wt. %.

For example, in one embodiment, the core may comprise a PLA having a lower % D isomer of polylactic acid than that of the % D isomer PLA polymer used in the sheath. The PLA polymer with lower % D isomer will show higher degree of stress induced crystallization during spinning while the PLA polymer with higher D % isomer will retain a more amorphous state during spinning. The more amorphous sheath will promote bonding while the core showing a higher degree of crystallization will provide strength to the fiber and thus to the final bonded web. In one particular embodiment, the Nature Works PLA Grade PLA 6752 with 4% D Isomer can be used as the sheath while NatureWorks Grade 6202 with 2% D Isomer can be used as the core.

In some embodiments, the fluid acquisition component may comprise sustainable polymer components of biodegradable products that are derived from an aliphatic component possessing one carboxylic acid group (or a polyester forming derivative thereof, such as an ester group) and one hydroxyl group (or a polyester forming derivative thereof, such as an ether group) or may be derived from a combination of an aliphatic component possessing two carboxylic acid groups (or a polyester forming derivative thereof, such as an ester group) with an aliphatic component possessing two hydroxyl groups (or a polyester forming derivative thereof, such as an ether group).

Additional nonlimiting examples of bio-based polymers include polymers directly produced from organisms, such as polyhydroxyalkanoates (e.g., poly(beta-hydroxyalkanoate), poly(3-hydroxybutyrate-co-3-hydroxyvalerate, NODAX™), and bacterial cellulose; polymers extracted from plants and biomass, such as polysaccharides and derivatives thereof (e.g., gums, cellulose, cellulose esters, chitin, chitosan, starch, chemically modified starch), proteins (e.g., zein, whey, gluten, collagen), lipids, lignins, and natural rubber; and current polymers derived from naturally sourced monomers and derivatives, such as bio-polyethylene, bio-polypropylene, polytrimethylene terephthalate, polylactic acid, NYLON 11, alkyd resins, succinic acid-based polyesters, and bio-polyethylene terephthalate.

In some embodiments, the fluid acquisition component staple fibers may comprise a bio-based polymer comprising a bio-based polyethylene that is derived from a biological source. For example, bio-based polyethylene can be prepared from sugars that are fermented to produce ethanol, which in turn is dehydrated to provide ethylene. An example of a suitable sugar cane derived polyethylene is available from Braskem S.A. under the product name PE SHA7260.

In some embodiments of the fluid acquisition component staple fibers, the sheath may comprise a bio-based polyethylene, and the core may comprise a PLA polymer.

In some embodiments, the sheath may comprise a PLA or PBS polymer and the core a synthetic polymer, such as polypropylene.

In some embodiments, the staple fibers of the fluid acquisition component may include one or more additives that are blended with the polymer(s) during the melt extrusion phase. Examples of suitable additives include one or more of molecular and/or gas filters, such as zeolites, ion-exchange particles, activated carbon, and the like, colorants, such as pigments (e.g., $TiO_2$), UV stabilizers, hydrophobic agents, hydrophilic agents, antistatic agent, elastomers, compatibilizers antioxidants, anti-block agent, slip agent, optical brighteners, flame retardants, antimicrobials, such as copper oxide and zinc oxide and the like.

Airlaid Nonwoven Component

As discussed above, the airlaid component comprises an airlaid nonwoven comprising a blend of non-cellulose staple fibers and bamboo derived staple fibers. In one embodiment, the airlaid component comprises a plurality of airlaid nonwoven layers in which one or more of the airlaid nonwoven layers comprises a blend of non-cellulose staple fibers and bamboo derived staple fibers. Preferably, when the airlaid nonwoven component comprises a plurality of airlaid nonwoven layers, each of the airlaid nonwoven layers comprises a blend of non-cellulose staple fibers and bamboo derived staple fibers.

As previously noted, the airlaid nonwoven component may be bonded to the fluid acquisition component using bonding techniques, such as thermal bonding (e.g., calender bonding or air through bonding), mechanical bonding (e.g., hydraulic entanglement or needle punching), chemical bonding (e.g., using an adhesive or other bonding resin), ultrasonic bonding, or the like. In a preferred embodiment, the airlaid nonwoven component is thermally bonded to the fluid acquisition component by passing the composite sheet material through an air through bonding unit in which the composite sheet material is exposed to a stream or streams of heated gas that is above the softening or melting temperature of at least one polymer component of the composite sheet material.

Suitable polymers, materials, additives, and properties for the non-cellulose staple fibers and the bamboo derived staple fibers are discussed previously in connection with the airlaid nonwoven.

Optional Coating Layers

Figure 5:
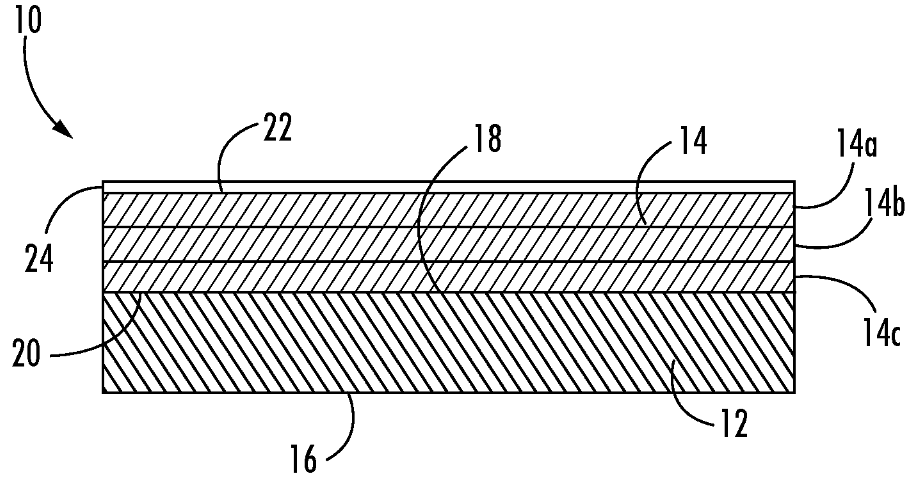
FIG. 5 is a cross-sectional side view of a composite sheet in accordance with at least one embodiment of the present invention in which the composite sheet includes a coating layer deposited on the surface of the outermost airlaid layer.

In some embodiments, the composite sheet may further comprise a polymer-based coating layer that is deposited on the outer surface 22 of the airlaid component. In this regard, FIG. 5 illustrates an embodiment of the invention in which the composite sheet material 10 comprises a coating layer 24 disposed on the outer surface of the airlaid component 14. In one embodiment, the coating layer may be applied a composition comprising a carrier, such as water or an organic solvent, and a polymeric material dispersed in the carrier. For example, in one embodiment, the coating layer may comprise a latex formulation of an aqueous polymer dispersion comprising ethylene vinyl acetate, acrylates, polyacrylates, phenylethylenes, butadienes, styrene butadiene-acrylic acids, polyvinyl alcohols, and mixtures thereof.

In one embodiment, the polymer-based layer comprises a bio-based latex of plant origin. Such a bio-based latex is available from OrganoClick under the tradename OC-BIO-BINDER™ Lily 1450. Other bio-based materials include carboxy methyl cellulose (CMC) and sodium carboxy methyl cellulose (Na CMC).

In one embodiment, the latex formulation comprises a polymer produced from the monomers vinyl acetate and ethylene, which is available from Wacker under the product name VINNAPAS® 192, with a solid constituent ranging from about 45 to 55%.

The coating layer may be applied to the composite sheet material in variety of different ways, such as, spray coating, foam coating, kiss coating, and the like.

In the case of an aqueous dispersion or emulsion, the coating layer is applied as a liquid, which is then dried and cured to form a solid coating adhered to the composite sheet. The amount of the coating layer added to the composite sheet, following any drying and cure step is typically from about 1 to 5 weight percent, and in particular, from about 1.5 to 3 weight percent, and more particularly, from about 1.75 to 2.25 weight percent, based on the total weight of the composite sheet.

In some embodiments, the optional coating layer, such as a latex, may be added onto opposite sides of the composite sheet material. In such cases, the add-on dried weight of the optional coating layer may be from about 2 to 10 weight percent, and in particular, from about 3 to 6 weight percent, and more particularly, from about 3.5 to 4.5 weight percent, based on the total weight of the composite sheet.

Process of Preparing the Composite Sheet

Figure 6A:
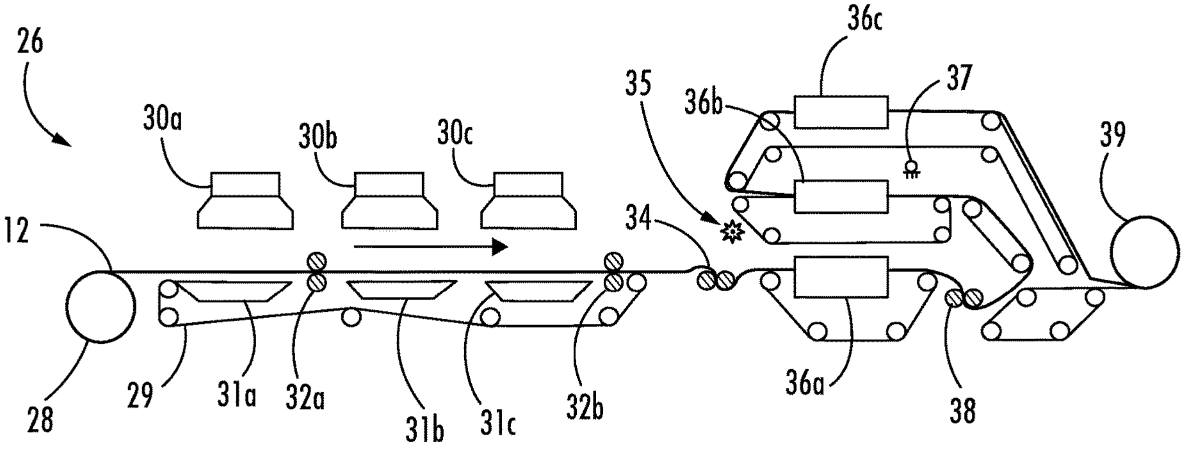
FIG. 6A is a schematic illustration of a system for preparing a composite sheet in accordance with an embodiment of the present invention.

With reference to FIG. 6A, a system and associated process for preparing the composite sheet material is shown and designated with reference character 26. The system 26 includes a source of fabric for use as the fluid acquisition layer 12. In the illustrated embodiment, the source is shown as a spool 28 on which the previously formed fluid acquisition layers is wound. However, it should be recognized that the system may include a fabric forming device, for example, a card or spinning beam, for preparing the nonwoven fabric of the fluid acquisition layer in a continuous line with respect to the rest of the system 26.

As shown, the nonwoven fabric of the fluid acquisition layer 12 is removed from the spool 28 and deposited on a collection surface 29, such as an endless belt. The fluid acquisition layer is then transported to a series of airlaid fabric forming heads (30*a*, 30*b*, 30*c*). At each forming head a stream of cellulose and non-cellulose staple fibers are homogeneously mixed to form a stream of mixed staple fibers. The first forming head then deposits the mixed stream of staple fibers onto the surface of the fluid acquisition layer 12, and the other forming heads each successively deposit an additional airlaid layer. A vacuum 31*a*, 31*b*, 31*c*, is positioned underneath the collection surface, and below each of the forming heads to assist in depositing the mixed stream of fibers onto the fluid acquisition layer 12. The system may optionally include one or more pairs of compaction rollers 32*a*, 32*b* that are disposed following each forming head. When present, compaction rollers 32*a*, 32*b* may be heated. For example, the compaction rollers 32*a*, 32*b* may be heated at a temperature ranging from about 90 to 110° C.

Although three airlaid forming heads are shown, it should be understood that the system may include any number of forming heads depending on the desired number of airlaid layers that are deposited onto the fluid acquisition layer 12. For example, the number of airlaid forming heads may range from 1 to 10, such as 2 to 8, 3 to 6, and 4 to 5. It should also be recognized that during operation of the system, one or more of the forming heads may not be used.

Figure 6B:
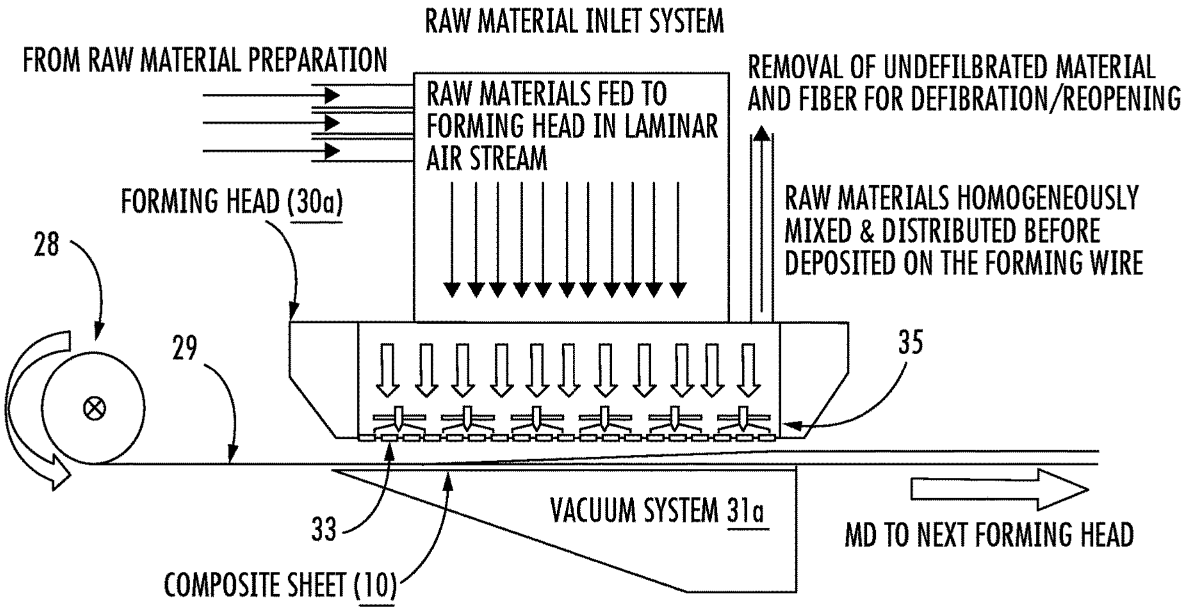
FIG. 6B shows a schematic illustration of a forming head for preparing an airlaid layer in accordance with at least one embodiment of the present invention.

With reference to FIG. 6B, a forming head that may be used in certain embodiments of the invention is illustrated. As can be seen, the forming head 30*a* includes a plurality of agitators 35 that create a turbulent flow within the forming head. The turbulent flow causes the cellulose and non-cellulose staple fibers to mix and form a homogenous mixture. The forming head also includes a screen 33 that limits/controls the output of the staple fibers from the forming head and thereby helps to form an evenly distributed airlaid layer.

Turning back to FIG. 6A, the composite sheet material with the thus deposited airlaid layers is transported to a first heating oven 36*a*. The first heating oven is typically maintained at a temperature that is sufficient to soften and melt the non-cellulose fibers of the airlaid layers. This melting causes the polymers to flow and fuse to adjacent fibers to provide a coherent composite sheet. For example, in embodiments in which the non-cellulose staple fibers comprised a bicomponent fiber having a polyethylene sheath, the composite sheet material may be heated to a temperature above the melting point of the sheath, but below the melting point of the core. For polyethylene, the temperature of the oven will typically be from about 120 to 165° C.

In some embodiments, the system may include one or more embossing rolls 34 that may be used to impart an embossed pattern on the surface of the composite sheet. In some embodiments, the system may also include a pair of calibration rolls 38 to adjust the thickness/profile of the composite sheet, and/or assist in interlayer bonding between adjacent layers. Calibration rolls 38 may define a nip or be gapped. In some embodiments, the calibration rolls are heated; in other embodiments, the calibration rolls are not heated.

Prior to this initial thermal bonding in the first heating oven, the composite sheet is transported to an application station 35 at which point a coating layer may be applied to the surface of the outermost airlaid layer. This coating layer may be applied using conventional techniques such as are known in the art including, spray coating, kiss roll application, and the like. In a preferred embodiment, a coating of an aqueous latex dispersion is applied to the surface of the composite web. In some embodiments, a second application coating layer may be applied to the opposite side of the coating via application station 37.

Following application of the optional second coating layer, or any other materials to the surface of the composite sheet, the composite sheet is transported to a second heating oven 36*b* that is maintained at a temperature that dries and cures the previously applied coating layers. Optionally, the composite sheet material may be further heated in a third oven 36*c*.

The bonded and dried composite sheet material may then be wound onto roll 39. In some embodiments, the composite sheet may be cut continuously in the machine direction to form a plurality of individual composite sheets that are each wound onto separate rolls.

Figure 7:
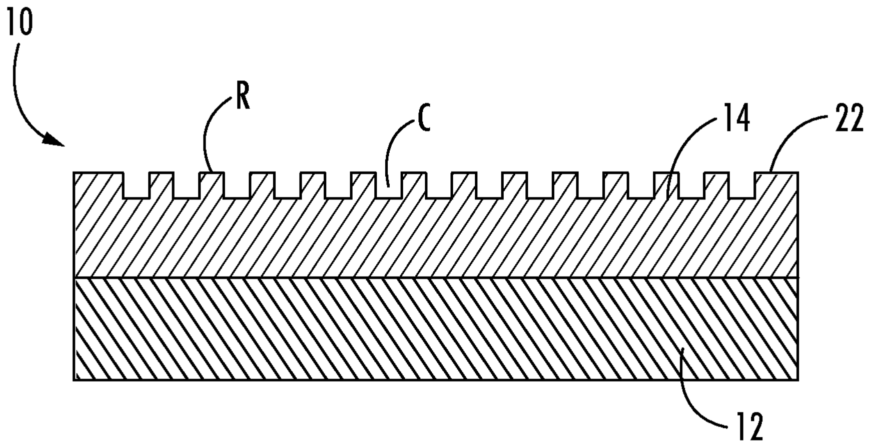
FIG. 7 is a cross-sectional side view of a composite sheet in accordance with at least one embodiment of the present invention in which the composite sheet includes a plurality of alternating ridges and channels formed on the surface of the outermost airlaid layer.

In some embodiments, it may be desirable to emboss a pattern onto the airlaid component of the composite sheet. For example, using the embossing roll 34 shown in FIG. 6A. In this regard, FIG. 7 shows an embodiment of the invention in which the surface 22 of the composite sheet 10 has a plurality of alternating ridges R and channels/grooves C that are defined on the surface of the outermost airlaid layer. In the construction of an absorbent article, the fluid acquisition layer is typically disposed towards the top sheet whereas the airlaid component is disposed towards the absorbent core. Fluid entering the composite sheet material is distributed through the fluid acquisition layer and into the airlaid layer(s). As it is transported towards the absorbent core, the plurality of ridges and channels helps to further distribute the fluid so that it may be more evenly distributed throughout the airlaid layer, and hence, throughout the absorbent core.

The pattern of alternating ridges and channels typically extend in the machine direction of the composite sheet material, but other orientations are possible, such as diagonally or in the cross direction, or in a nonlinear, such as serpentine, and/or noncontinuous configuration.

The pattern may be produced by a roll in which having a pattern of alternating raised surfaces and grooves that extend circumferentially about the roll. In some embodiments, the roll may be heated and pressure may be applied to the surface of the composite sheet material to help facilitate formation of the pattern of alternating grooves and ridges. The widths of each groove (e.g., distance between adjacent ridges) may vary depending upon the intended application of the absorbent article, but will typically range from about 0.2 to 10 mm, and in particular, from about 1 to 6 mm, and more particularly, from about 2 to 3 mm. The depth of each groove will typically be about 0.1 to 5 mm, and in particular, from about 0.3 to 3 mm.

Figure 8:
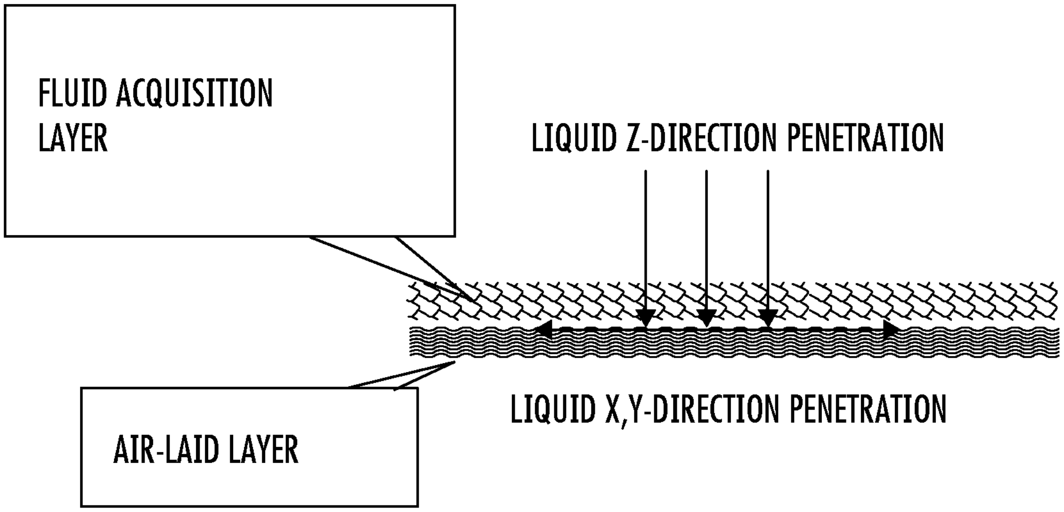
FIG. 8 depicts fluid transport and distribution through a composite sheet material.

As discussed previously, the composite sheet material of the present invention is particularly useful as a transfer layer, such an AQDL component, in absorbent articles. In particular, the composite sheet is able to rapidly transport fluids through the fluid acquisition layer and then distribute the fluid laterally through the one or more airlaid layers. This transport of fluid is illustrated in FIG. 8.

Absorbent Core of an Absorbent Article

In some embodiments of the invention, the inventive airlaid nonwoven may comprise a component of the absorbent core of an absorbent article. In such an embodiment, the airlaid nonwoven may comprise a plurality of airlaid nonwoven layers in accordance with embodiments of the invention. In particular, the absorbent core may include from 1 to 10 airlaid nonwoven layers.

In addition, the airlaid nonwoven for use in an absorbent core may comprises one or more of the previously described non-cellulose staple fibers. For example, the non-cellulose staple fibers may comprise polymers derived from synthetic polymers, such as polyolefins, polyesters, polyamides, such as nylons, and the like, and combinations and blends thereof. In some embodiments, the non-cellulose staple fibers may comprise polymers derived bio-based polymers, such as PLA, PBS, green polyolefins, such as green polyethylene, green polyesters, such as green polyethylene terephthalate, combinations of one or more bio-based polymers, and blends of one or more bio-based polymers. Suitable examples of bio-based polymers are discussed previously.

In addition, the non-cellulose staple fibers may comprise combinations and/or blends of polymers derived from synthetic polymers and bio-based polymers.

As previously discussed, the non-cellulose staple fibers may comprise monocomponent or multicomponent fibers, or a mixture of monocomponent and multicomponent fibers.

In absorbent core applications, the airlaid nonwoven or, collectively, plurality of airlaid nonwoven layers will typically have a basis weight ranging from about 25 to 400 gsm and a thickness ranging from about 0.4 to 4 mm.

In addition to the inventive airlaid nonwoven, the absorbent core may include a superabsorbent polymers. Suitable absorbent polymers are discussed previously. When present, the SAP may be present in an amount from 10 to 90 weight percent, based on the total weight of the absorbent core.

In certain embodiments, an absorbent core in accordance with one more embodiments of the invention may comprise both non-cellulose staple fibers and cellulosic fibers comprising bamboo derived fibers. In some embodiments, the cellulosic fibers comprise a mixture of bamboo derived fibers and conventional wood pulp fibers.

Typically, the amount of bamboo derived fibers in the absorbent core is from 5 to 100 weight percent, based on the total weight of the absorbent core. In a preferred embodiment, the amount the amount of bamboo derived fibers in the absorbent core is from about 75 to 100 weight percent, based on the total weight of the absorbent core, with an amount from 85 to 100 weight percent, being somewhat more preferred.

In certain embodiments, the amount of bamboo derived fibers in the absorbent core is about 5 weight percent or greater, about 10 weight percent or greater, about 15 weight percent or greater, about 20 weight percent or greater, about 25 weight percent or greater, about 30 weight percent or greater, about 35 weight percent or greater, about 40 weight percent or greater, about 45 weight percent or greater, about 50 weight percent or greater, about 55 weight percent or greater, about 60 weight percent or greater, about 65 weight percent or greater, about 70 weight percent or greater, about 75 weight percent or greater, about 80 weight percent or greater, about 85 weight percent or greater, about 90 weight percent or greater, about 95 weight percent or greater, about 96 weight percent or greater, about 97 weight percent or greater, about 98 weight percent or greater, or about 99 weight percent or greater, based on the total weight of the absorbent core.

In certain embodiments, the amount of bamboo derived fibers in the absorbent core is about 100 weight percent or less, about 99 weight percent or less, about 98 weight percent or less, about 97 weight percent or less, about 96 weight percent or less, about 95 weight percent or less, about 90 weight percent or less, about 85 weight percent or less, about 80 weight percent or less, about 75 weight percent or less, about 70 weight percent or less, about 65 weight percent or less, about 60 weight percent or less, about 55 weight percent or less, about 50 weight percent or less, about 45 weight percent or less, about 40 weight percent or less, about 35 weight percent or less, about 30 weight percent or less, about 25 weight percent or less, about 20 weight percent or less, about 15 weight percent or less, about 10 weight percent or less, about 5 weight percent, based on the total weight of the absorbent core.

In certain embodiments, absorbent cores comprising airlaid nonwovens in accordance with embodiment the invention exhibit a decrease in thickness (caliper) ranging from 10 to 60%, and in particular, from about 20 to 50%, and more particularly, from 25 to 45% in comparison to a similar airlaid nonwoven in which the similar airlaid nonwoven comprises staple fibers comprising conventional wood pulp fibers in lieu of bamboo derived staple fibers.

In certain embodiments, the absorbent core comprises at least one airlaid nonwoven layer comprising a blend of non-cellulose staple fibers and bamboo derived fibers. In this embodiment, the bamboo derived fibers provide absorbency while the non-cellulose fibers provide integrity and structural support for the absorbent core. The absorbent core comprising a blend of non-cellulose staple fibers and bamboo derived staple fibers may be thermally bonded via one or more of calender bonding, air through thermal bonding, or a combination thereof.

In embodiments comprising non-cellulose staple fibers, the amount of non-cellulose staple fibers in the absorbent core is typically from about 1 to 30 weight percent, based on the total weight of the core, and in particular, from about 2 to 20 weight percent, based on the total weight of the absorbent core. In a preferred embodiment, he amount of non-cellulose staple fibers in the absorbent core is typically from about 3 to 10 weight percent, based on the total weight of the absorbent core, and more preferably, from about 4 to 6 weight percent, based on the total weight of the absorbent core.

In certain embodiments, the amount of non-cellulose staple fibers in the absorbent core is about 1 weight percent or greater, about 2 weight percent or greater, about 3 weight percent or greater, about 4 weight percent or greater, about 5 weight percent or greater, about 6 weight percent or greater, about 7 weight percent or greater, about 8 weight percent or greater, about 9 weight percent or greater, about 10 weight percent or greater, about 11 weight percent or greater, about 12 weight percent or greater, about 13 weight percent or greater, about 14 weight percent or greater, about 15 weight percent or greater, about 16 weight percent or greater, about 17 weight percent or greater, about 18 weight percent or greater, about 19 weight percent or greater, about 20 weight percent or greater, about 21 weight percent or greater, about 22 weight percent or greater, or about 23 weight percent or greater, about 24 weight percent or greater, about 25 weight percent or greater, about 26 weight percent or greater, about 27 weight percent or greater, about 28 weight percent or greater, about 29 weight percent or greater, or about 30 weight percent or greater, based on the total weight of the absorbent core.

In certain embodiments, the amount of non-cellulose staple fibers in the absorbent core is about 30 weight percent or less, about 29 weight percent or less, about 28 weight percent or less, about 27 weight percent or less, about 26 weight percent or less, about 25 weight percent or less, about 24 weight percent or less, about 23 weight percent or less, about 22 weight percent or less, about 21 weight percent or less, about 20 weight percent or less, about 19 weight percent or less, about 18 weight percent or less, about 17 weight percent or less, about 16 weight percent or less, about 15 weight percent or less, about 14 weight percent or less, about 13 weight percent or less, about 12 weight percent or less, about 11 weight percent or less, about 10 weight percent or less, about 9 weight percent or less, about 8 weight percent or less, about 7 weight percent, about 6 weight percent or less, about 5 weight percent or less, about 4 weight percent or less, about 3 weight percent or less, about 2 weight percent or less, or about 1 weight percent or less, based on the total weight of the absorbent core.

In certain other embodiments, the absorbent core comprising at least one airlaid nonwoven layer may include no or substantially no non-cellulose staple fibers. For example, in some embodiments, the cellulose fibers of the absorbent core may be bonded via a latex material or may be bonded via hydrogen bonding.

Suitable latex materials may be derived from synthetic materials or bio-based materials. Examples of suitable latex materials are discussed previously. Typically, the amount of latex material used to bond the absorbent core is from about 0.5 to 15 weight percent, based on the total weight of the absorbent core. In certain embodiments, the latex is present, based on an add-on dried weight amount, from about 1.5 to 20 weight percent, based on the total weight of the absorbent core. At weight percentages above 6 weight percent, the latex material is typically used for a latex bonded absorbent core.

In certain embodiments, the absorbent core may comprise a blend of non-cellulose staple fibers and latex for bonding the cellulose fibers.

In certain embodiments, the one or more airlaid nonwoven layers may include a tissue layer. In one embodiment, the one or more airlaid nonwoven layers may be sandwiched between a pair of tissue layers. The tissue layers may comprise tissue derived from bamboo fibers, conventional wood pulp fibers, and mixtures thereof.

Absorbent Articles

Composite sheets in accordance with the present invention may be used in a wide variety of different articles, and in particular, a wide variety of absorbent articles.

Figure 9:
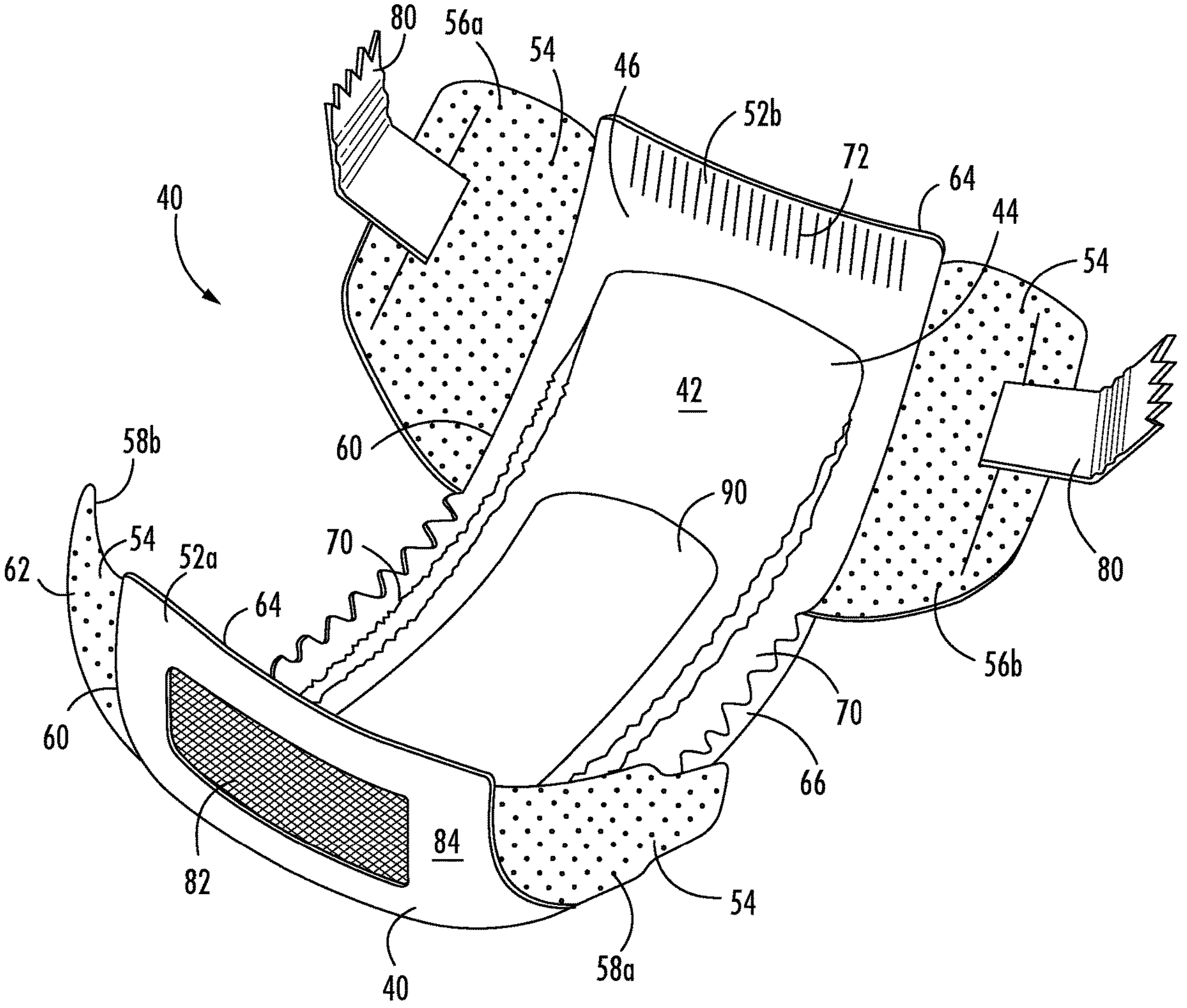
FIG. 9 is an illustration of an absorbent article in accordance with at least one embodiment of the present invention.

With reference to FIG. 9, an embodiment of an absorbent article ("diaper") in accordance with embodiments of the present invention is shown and broadly designated by reference number 40. The diaper 40 includes a core region 42 in which an absorbent core 44 is disposed. A chassis region 46 surrounds the core region 42, and includes a front 48, back 50, and front and back waist regions 52*a*, 52*b*. The chassis region comprised of front, back and core regions generally has a composite structure comprising a liquid permeable topsheet and a liquid impermeable backsheet that are attached to each other along opposing surfaces to define a cavity there between in which the absorbent core is disposed.

Suitable materials for the topsheet, backsheet, and absorbent core may generally comprise any materials conventionally used in the manufacture of absorbent articles.

As shown in FIG. 9, the diaper also includes a composite sheet material 10 (see FIG. 3) in accordance with at least one embodiment of the present invention. The composite sheet 10 defines a fluid transport layer, such as a fluid acquisition distribution system 90 (i.e., AQDL component) of the absorbent article. As discussed above, the composite sheet 10 defines a fluid distribution/acquisition component that helps to efficiently facilitate transfer of fluid from the wearer to the absorbent core 44.

In some embodiments, the front and back regions of the diaper also each includes a pair of ears 54 that are disposed in the waist regions of the diaper. (As used herein, the term "disposed" is used to mean that an element(s) of the diaper is formed (joined and positioned) in a particular place or position as a unitary structure with other elements of the diaper or as a separate element joined to another element of the diaper.) The ears 54 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract.

In addition, the ears 54 develop and maintain wearing forces (tensions) that enhance the tensions developed and maintained by a fastening system, discussed in greater detail below, to maintain the diaper 40 on the wearer and enhance the waist fit. As shown in FIG. 9, the diaper includes a pair of back ears 56*a*, 56*b* which are joined to the back region 50 of the diaper chassis proximate to the back waist region 52*b*, and a pair of front ears 58*a*, 58*b*, which are joined to the front region 48 of the diaper chassis proximate of the front waist region 52*a*.

The front and back ears may be joined to the chassis region 46 by any bonding method known in the art such as adhesive bonding, pressure bonding, heat bonding, and the like. In other embodiments, the front and/or back ears may comprise a discrete element joined to the chassis region with the chassis region 46 having a layer, element, or substrate that extends over the front and/or back ear. For example, each ear may comprise a portion of the diaper chassis region that extends laterally outwardly from and along the side edge 60 of the chassis region to a longitudinal edge 62 of the diaper 40. In one embodiment, the ears generally extend longitudinally from the end edge 64 of the diaper 40 to the portion of the longitudinal edge 62 of the diaper 20 that forms the leg opening (this segment of the longitudinal edge 62 being designated as leg edge 66). In some embodiments, the ears may comprise a separate fabric or web that has been joined to the topsheet or the backsheet. In other embodiments, each ear may be formed by the portions of the topsheet and the backsheet that extend beyond the side edges of the absorbent core 44.

In one embodiment, the diaper 40 may also include elastic leg cuffs 70 for providing improved containment of fluids and other body exudates. Each elasticized leg cuff 70 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled “Contractable Side Portions for a Disposable Diaper” issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled “Disposable Absorbent Article Having Elasticized Flaps” issued to Aziz and Blaney on Mar. 20, 1990, describes a disposable diaper having “stand-up” elasticized flaps (barrier cuffs) to improve the containment of the leg regions. U.S. Pat. No. 4,695,278 entitled “Absorbent Article Having Dual Cuffs” issued to Lawson on Sep. 22, 1987, describes a disposable diaper having dual cuffs including a gasketing cuff and a barrier cuff. U.S. Pat. No. 4,704,115 entitled “Disposable Waist Containment Garment” issued to Buell on Nov. 3, 1987, discloses a disposable diaper or incontinent garment having side-edge-leakage-guard gutters configured to contain free liquids within the garment. Each of these patents are incorporated herein by reference. U.S. Pat. No. 6,476,289 entitled “Garment Having Elastomeric Laminate” describes various elastic leg cuff configurations that may also be used in embodiments of the present invention.

In a preferred embodiment, the leg cuffs may comprises a fabric layer having an SMS structure comprising a plurality of elastic strands that are incorporated into the leg cuff structure. Preferably, the leg cuffs comprises a material having liquid barrier properties.

One example of a fabric for use in forming leg cuffs comprises an SMS fabric having a spunbond nonwoven layer comprising bicomponent fibers having a first polymer component sheath and a second polymer component core. Examples of materials for the sheath and core include polyolefins, such as polypropylene and polyethylene, polyesters, PLA based polymers, and the like. In one embodiment, the bicomponent fibers comprise a polypropylene sheath, and a PLA core. An example of a polypropylene material for use in this embodiment may have a melt flow rate (MFR) between 20 to 40 g/10 min (measured in accordance with ASTM D1238 (190° C./2.16 kg)) such as, for example, provided by Total Petrochemicals and Refining USA, Inc. of La Port, TX, 77571 USA as grades M 3766 (metallocene polypropylene) and 3764 or 3866 (Zeigler Natta polypropylene). A suitable material for use as the PLA core is available from Nature Works PLA as Grade 6202 with 2% D Isomer. The meltblown layer may comprise a polypropylene having an MFR of 1,300 g/10 min (measured in accordance with ASTM D1238 (190° C./2.16 kg)) such as, for example, provided by Total Petrochemicals and Refining USA, Inc. of La Port, TX, 77571 USA as grade 3962.

In a second example, the leg cuffs may comprise an SMS fabric having a spunbond nonwoven layer comprising bicomponent fibers having a PLA sheath and a PLA core, and a meltblown layer comprising PLA fibers. An example of a suitable PLA material for use as the sheath is PLA grade 6752 with 4% D Isomer, and an example of a suitable PLA material for use as the core is PLA grade 6202 with 2% D Isomer, both of which are available from NatureWorks. A suitable material for the PLA meltblown fibers is PLA grade 6252, which is also available from NatureWorks.

In a third embodiment, the leg cuffs may comprise a fabric having an SMS structure in which the spunbond nonwoven layers comprise a bicomponent fabric having a polypropylene sheath and a PLA core. Examples of suitable materials for the sheath and core are described above. The meltblown layer may comprise meltblown fibers comprising a blend of PLA and polypropylene that has been reclaimed from spunbond bicomponent fibers comprised of PP/PLA using the process taught in International Application PCT/US 2015/012658.

In a fourth embodiment, the leg cuffs may comprise a fabric having an SMS structure in which the spunbond nonwoven layers comprise a bicomponent fabric having a PLA sheath and a PLA core. Examples of suitable materials for the sheath and core are described above. As in the third embodiment discussed above, the meltblown layer may comprise meltblown fibers comprising a blend of PLA and polypropylene that has been reclaimed from spunbond bicomponent fibers comprised of PP/PLA using the process taught in International Application No. PCT/US2015/012658.

Preferably, spunbond fabrics for forming the leg cuffs have a sheath/core ratio of approximately 30/70 to 70/30. In one embodiment, the basis weight of the SMS fabric is between about 8 g/m$^2$ and 15 g/m$^2$. Preferably, the meltblown content comprises about 10 to 30 weight %, based on the total weight of the SMS fabric. In some embodiments, the SMS fabric for use in forming the leg cuffs has a hydrohead value of greater than about 50 mm as measured in accordance with INDA Test Method WSP 80.6.

In some embodiments, the diaper 40 may also include elastic elements that are disposed around one or more of the waist region 52 and the elastic cuffs. For example, the diaper may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595; 4,710,189; 5,151,092; and 5,221,274.

In some embodiments, the elastic features may comprise elastic elements comprising elastic strands or threads that are contractably affixed between the topsheet and backsheet of the diaper. Such strands or threads can be comprised of a bio-based material, such as natural rubber. As noted above the natural rubber strands are covered by nonwoven, such as the topsheet and/or backsheet to ensure elastic component does not directly contact the wearer's skin.

The absorbent article may include a fastening system. The fastening system can be used to provide lateral tensions about the circumference of the absorbent article to hold the absorbent article on the wearer as is typical for taped diapers. This fastening system is not necessary for pull on style of absorbent articles, such as training pants or adult incontinence absorbent articles, since the waist region of these articles is already bonded.

The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. When fastened, the fastening system interconnects the front waist region **52*a* and the back waist region 52*b*. When fastened, the diaper 44** contains a circumscribing waist opening and two circumscribing leg openings.

The fastening system may comprise an engaging member 80 and a receiving member 82 (also referred to as a landing zone). The engaging member 80 may comprise hooks, loops, an adhesive, a cohesive, a tab, or other fastening mechanism. The receiving member 82 may comprise hooks, loops, a slot, an adhesive, a cohesive, or other fastening mechanism that can receive the engaging member 80. Suitable engaging member 80 and receiving member 82 combinations are well known in the art and include but are not limited to hooks/loop, hooks/hooks, adhesive/polymeric film, cohesive/cohesive, adhesive/adhesive, tab/slot, and button/button hole. Suitably, the fastening system may comprise a polymer derived from a bio-based material.

In this regard, FIG. 9 further shows a fastening system in which the engaging member comprises a pair of tabs 80 that are joined to the back ears 56*a*, 56*b*, and an associated landing zone 82 disposed on a front surface 84 of the diaper 40. In some embodiments, the tabs may include a pressure sensitive adhesive for adhesively attaching the tabs to the landing zone.

Some exemplary surface fastening systems are disclosed in U.S. Pat. Nos. 3,848,594; 4,662,875; 4,846,815; 4,894,060; 4,946,527; 5,151,092; and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; and 5,591,152.

In a preferred embodiment, the fastening system can employ a hook and loop as described in U.S. Pat. No. 9,084,701. In a preferred embodiment, the hook and loop fastening system comprises a female fastening material made of fibrous material and a male fastening material with hooks configured for the fibrous material.

In one embodiment, the female loop material comprises bonded bicomponent fibers comprising a bio-based material, such as spunbond bicomponent fibers having a PLA, and a sheath comprising a sugar cane derived polyethylene polymer. Examples of such materials are described above. An example of a suitable PLA polymer for the core in is available from NatureWorks as PLA Grade 6202.

A second fiber for use as the female loop component providing 50 bio-based material content comprises a sheath of petroleum based polypropylene polymer and a PLA core derived from NatureWorks under the product name PLA Grade 6202. Preferred polypropylenes for use in this embodiment will typically have a melt flow rate (MFR) between 20 to 40 g/10 min (measured in accordance with ASTM D1238 (190° C./2.16 kg)) such as for example provided by Total Petrochemicals and Refining USA, Inc. of La Port, TX, 77571 USA as grades M 3766 (metallocene polypropylene) and 3764 or 3866 (Zeigler Natta polypropylene).

A further example of fibers for constructing a female loop material, providing 50% bio-based material content, comprise spunbond bicomponent fibers in which the core comprises a lignin based polymer and a sheath comprising a petroleum based polyethylene. Such fibers are disclosed as examples 4, 5, 6, 7, 8, and 9 in European Patent No. EP 2,630,285 B1 and U.S. Patent Publication No. 2014/0087618.

Substitution of the petroleum based polyethylene sheath in these examples with a sheath comprised of either the sugar cane derived polyethylene available from Braskem S.A. or the corn derived PLA available from NatureWorks, both polymers disclosed above, would provide fibers having up to a 100% bio-based material content.

A further example of a fiber that can be used for constructing the female loop material is a bicomponent fiber having a core of (PLA), and a sheath comprising PLA. For example, in one embodiment, the core may comprise a PLA having a lower % D isomer of polylactic acid than that of the % D isomer PLA polymer used in the sheath. The PLA polymer with lower % D isomer will show higher degree of stress induced crystallization during spinning while the PLA polymer with higher D % isomer will retain a more amorphous state during spinning. The more amorphous sheath will promote bonding will the core showing a higher degree of crystallization will provide straight to the fiber and thus to the final bonded web.

In one particular embodiment, the Nature Works PLA Grade PLA 6752 with 4% D Isomer can be used as the sheath while NatureWorks Grade 6202 with 2% D Isomer can be used as the core.

A further example of fibers for use in the female loop material, providing at least 50% bio-based material content may comprise a 50/50blend of cotton fibers and a petroleum based polymer, such as polypropylene. Examples of polypropylene staple fibers useful to form such fabrics are available from Fibervisions Corporation as Grade T-198. Examples of cotton fibers for use to form such nonwoven fabrics include fibers sold under the product name TRUE-COTTON® available from TJ Beall Company, and fibers sold under the product name HIGH-Q ULTRA® available from Barnhardt Manufacturing Company.

The male hooks use in this fastening stem for the preferred embodiment are also comprised of significant sustainable content. The male fastening material including the hooks can be made by casting, molding, profile extrusion, or microreplications where the polymer used is corn derived PLA such as is available from NatureWorks. NatureWorks provides a selection of grades for injection molding that could be used to make such hooks including Grades 3001D, 3052D, 3100HP and 3251D.

Figure 10:
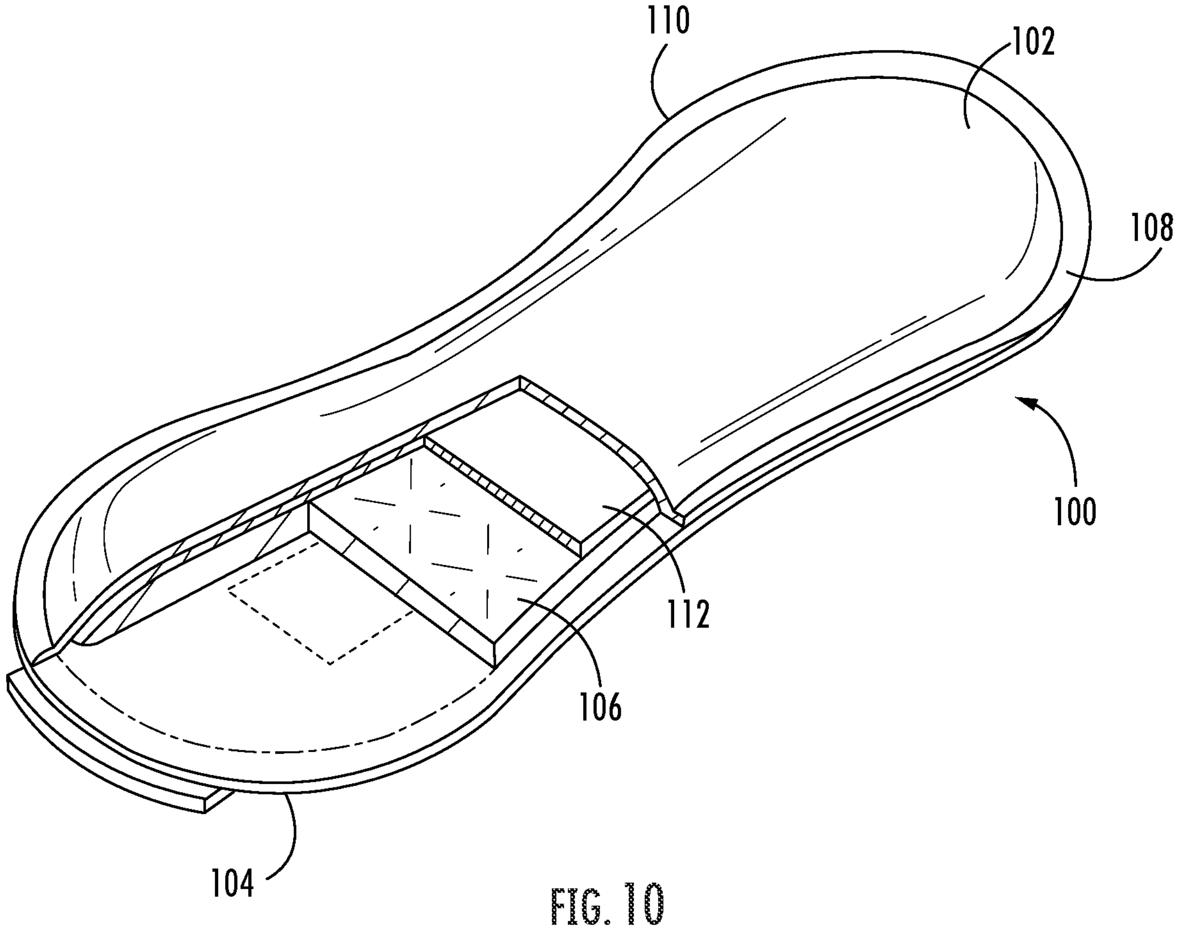
FIG. 10 is an illustration of an absorbent article in accordance with at least one embodiment of the present invention in which the absorbent article is in the form of a feminine sanitary pad.

With reference to FIG. 10, a further embodiment of an absorbent article in accordance with an embodiment of the present invention is illustrated in which the absorbent article is in the form of a feminine sanitary pad, broadly designated by reference character 100.

Pad 100 may include a topsheet 102, backsheet 104, and an absorbent core 106 disposed there between. Preferably, topsheet 102 and backsheet 104 are joined to each other about along opposing outer edges to define a continuous seam 108 that extends about the periphery 110 of the pad 100. Continuous seam 108 may comprise a heat seal that is formed from thermally bonding the topsheet and backsheet to each other. In other embodiments, continuous seam 108 is formed by adhesively bonding the topsheet and backsheet to each other.

Suitable materials for the topsheet, backsheet, and absorbent core may comprise materials typically used in the construction of absorbent articles.

As shown, pad 100 includes a composite sheet 10 (see FIG. 3) defining a fluid transport layer, such as a fluid AQDL component 112. The AQDL component is disposed between the absorbent core 106 and the topsheet 102. As discussed above, the composite sheet defining the fluid distribution/acquisition component comprises a fluid acquisition layer comprising a carded nonwoven and at least one airlaid layer comprising a blend of cellulose staple fibers and non-cellulose fibers, in which the fibers of the layers are thermally bonded to each other.

Various components of the absorbent article are typically joined via thermal or adhesive bonding. Examples of suitable adhesives include polyethylene, polypropylene, or ethylene vinyl acetate based melt adhesives. In some embodiments, the adhesive may comprise a bio-based adhesive. An example of a bio-based adhesive is a pressure sensitive adhesive available from Danimer Scientific under the product code 92721.

In yet another aspect, certain embodiments of the invention provide absorbent articles. In accordance with certain embodiments, the absorbent article may include a composite sheet in accordance with the present invention In this regard, composite sheets prepared in accordance with embodiments of the invention may be used in wide variety of articles and applications. For instance, embodiments of the invention may be used for personal care applications, for example products for babycare (diapers, wipes), for femcare (pads and liners), for adult care (incontinence products), or for cosmetic applications (pads).

EXAMPLES

The following examples are provided for illustrating one or more embodiments of the present invention and should not be construed as limiting the invention.

Unless otherwise defined, the technical terms used in the following embodiments have the same meaning as commonly understood by those skilled in the art to which this invention pertains. The test reagents used in the following embodiments, unless otherwise specified, are conventional reagents; the said experimental methods, unless otherwise specified, are conventional methods.

Test Methods

Thickness (caliper) was determined in accordance with EDANA 30.5-99 using a digital thickness tester. In accordance with this test, a sample of material is positioned between two plates under a pressure (0.5 kPa), and the distance between the two plates is reported in units of "mm."

Carry out sample taking and cutting according to different product requirements, the size edge of sample to be tested to the edge of the upper side of the instrument should not be less than 5 mm; the sample should be acclimated for at least 4 hours under constant temperature and humidity condition (23±2° C.; relative Humidity: 50%±5%). If acclimation of the sample will not be carried out, the temperature and humidity at that moment should be recorded while performing measurement, only for reference of comparison.

Basis Weight

Basis weight was measured in accordance with EDANA 40.3-90.

Mass determination: the mass of unit area is the mass determination of the sample (gram weight), with unit of $g/m^2$.

Tester: electronic balance (accuracy to 0.001 gram), screens are set around the balance to prevent air flow and other interference factors from impacting the balance.

The samples are required to balance for at least 4 hours under constant temperature and humidity condition (23±2° C.; relative Humidity: 50%±5%). If the balance will not be carried out for the on-line real-time test, the temperature and humidity at that moment should be recorded while performing measurement, only for reference of comparison.

Place the sample to be tested on the balance, after the reading of the balance becomes stable, record the weight in units of grams.

Mass determination (GSM)==AB

Where: GSM: the determined mass of a sample;

A: weight of a sample;

B: area of a sample.

Tensile strength and elongation at break were measured in accordance with EDANA 20.2-89.

Tensile strength: the tension required to pull a sample with specified size to break at constant speed. The percentage of the length when the sample is pulled to break to the original length of the sample is the elongation at breaking, in unit of "%".

Tester: Zwick 2.5 strength tester

Cut the sample to a size of 200 mm×25.4 mm, the sample is required to acclimate for at least 4 hours under constant temperature and humidity condition (23±2° C.; relative Humidity: 50%±5%). If acclimation is not done for on-line real-time test, the temperature and humidity at that moment should be recorded while performing measurement, only for reference of comparison.

Set the testing procedure according to following test parameters:

Maximum test limit: 100 N;

Test speed: 254 mm/min;

Clamping distance: 51 mm;

Clamping pressure: 5 bars.

Fluid Retention was measured in accordance with EDANA 10.4-02.

Liquid absorption capability: after soaking the sample in liquid for a time duration of 10 minutes, the percentage of total weight increase is the absorption capability of the sample.

Liquid absorption capability: after soaking the sample in liquid for a time duration of 10 minutes, the total weight increase is the absorption capability of the sample. (g/g)

Retention: after soaking the sample in liquid for a time duration of 10 minutes, and keep it in a container for 2 minutes, then carefully place a 1976 g weight on the sample, the weight increase is the water retaining capacity of the sample. (g/g)

Rewet (g)

Place the sample to be tested on the absorption core (the 150 gsm SAP core (18% SAP) is applied during the test). Place a φ60 mm cylinder at the center position of the sample to be tested, take 15 ml brine and put it into the cylinder, and start the time counting at the same time, after 5 minutes, place many layers of filter paper with known weight on the surface of sample (till the top layer of filter paper does not absorb any liquid), and place a 1.2 kg standard pressing block on the filter paper at the same time, start to count the time again, remove the standard pressing block after a duration of 1 minute, weigh the mass of filter paper on the sample surface by means of a balance, its increased weight is the reverse osmosis value. The smaller the value, the better rewet performance will be expected.

Fluid Acquisition was measured in accordance with EDANA 150.5-02.

Acquisition: when 5 ml 0.9% sodium chloride solution penetrates the sample, record the transit time of the liquid by circuit conductivity, in unit of second.

Tester: Lister liquid penetration instrument.

Wicking rate and Vertical Wicking Height: were measured in accordance with reference standard: EDANA 10.3-99.

After one end of vertically suspended sample is soaked in the liquid for 5 minutes, the height that the liquid rises along the sample is the suction range of the sample.

Sample size: the sample size is 30 mm×200 mm.

The sample is required to balance for at least 4 hours under constant temperature and humidity condition (23±2° C.; relative Humidity: 50%±5%).

Place the test stand into a plastic container, secure two rulers on the stand vertically, add 0.9% NaCl solution or distilled water (upon customer's request), adjust the liquid level to the scales on two rulers become 15 mm. Add and mix proper amount of blue coloring agent in the solution so as to make it easy to read. Rotate the rulers out of the liquid level, and wipe clean the water on the surface, fix the well prepared sample on the rulers by using fish tail clips, pay attention to align the lower end of the ruler with the zero point. Rotate the rulers out of the liquid level, and start count the time at the same time. Incline the end of the ruler extended into the liquid slightly backward to allow a certain gap between the ruler and the sample. At the same time the timer sounds after five minutes, rotate two rulers out of the liquid level and read the readings (observe the height that the liquid rises along the sample, read the value at peak point, if the individual value is too high on the sample edge, round it and read the value at other peak point). The test result is the actual value is subtracted by 15 mm, to provide the wicking rate.

For vertical wicking rate, the above procedures are used except that the fluid height is measured after 15 seconds.

The materials used in the composite sheets and comparative nonwoven fabrics are identified below. All percentages are weight percents unless indicated otherwise. All physical property and compositional values are approximate unless indicated otherwise.

"Pulp-1" refers to a treated pulp staple fiber derived from bamboo and available from TAISON under the product name Bamboo Fluff. The bamboo staple fibers had average lengths of 1.7 mm and average widths of approximately 18 microns. The bamboo staple fibers were prepared via pulping from clumping bamboo predominately comprising a blend of the bamboo species *Neosino calamus affinis, Lingnania intermedia, Bambusa rigida Keng et Keng f.*, and *Bambusa oldhamii*. Prior to pulping the bamboo fibers had the following properties:

- average length of 2.37 mm;
- average width of 16.6 microns;
- length to width ratio of 145;
- wall thickness to cavity ratio of 1.7; and
- a cellulose content of 48.08 weight percent and lignin content of 26 weight percent.

"Pulp-2" refers to a conventional treated pulp staple fiber available from Georgia Pacific under the product name 4722.

"PE/PET-1" refers to bicomponent staple fibers having a polyethylene sheath and a polyethylene terephthalate core, a fineness of 2.2 dtex, and an average length of 4 mm, which are available from Toray Chemical Korea Inc. under the product name FDL 17360.

"PE/PET-2" refers to bicomponent staple fibers having a polyethylene sheath and a polyethylene terephthalate core, having a fineness of 2.2 dtex, and an average length of 38 mm, which are available from Huvis under the product designation N81S.

"Latex" refers to an aqueous polymer dispersion produced from the monomers vinyl acetate and ethylene, which is available from Wacker under the product name VINNAPAS® 192. The Latex formulation was diluted with water to have a solid constituent ranging from 14 to 20%.

In the Inventive Examples set forth below, composite sheets in accordance with embodiments of the present invention were prepared by depositing 2 airlaid fabric layers overlying an air through bonded (ATB) carded fabric layer. The carded ATB fabrics used in Inventive Example 1 and Comparative Example 1 is as follows.

"ATB-1" refers to a carded fabric comprising staple fibers of PE/PET-2. The carded fabric had a basis weight of 20 $g/m^2$.

Preparation of Example 1 and Comparative Example 1

Unless otherwise indicated, the inventive examples were prepared according to the following procedures. In a first step, a previously prepared a fabric comprised of an air through bonded, carded nonwoven fabric (ATB-1 fabric) was provided an unwound from a spool and transferred onto a continuous mesh belt. This ATB fabric defines the fluid acquisition layer, and hence, the fluid distribution component, of the composite sheet.

In Inventive Example 1, the ATB-1 fabric was transported to the airlaid forming heads which deposit a mixture of non-cellulose (PET-1) and bamboo derived staple fibers (Pulp-1) onto the ATB fabric to form airlaid component of the composite sheet.

In Comparative Example 1, the ATB-1 fabric was transported to the airlaid forming heads which deposit a mixture of non-cellulose (PET-1) and cellulose staple fibers (Pulp-2) onto the ATB fabric to form airlaid component of the composite sheet.

In Inventive Example 1 and Comparative Example 1, 2 airlaid layers were deposited overlying the ATB fabric. The airlaid fabric layers were formed with a horizontal screen type forming technology with airlaid equipment obtained from M&J Company. The resulting basis weight of the composite sheet material for both Inventive Example 1 and Comparative Example 1 was approximately 80 gsm.

In the airlaid process, cellulose staple fibers and non-cellulose fibers of the airlaid layer(s) were homogeneously mixed using an air stream and a plurality of blades that create a turbulent flow within each forming head. A vacuum is positioned under the belt to assist in collecting the staple fibers onto the surface of the ATB fabric layer. After a first airlaid layer was deposited, a compaction roller was optionally positioned between the first and second forming heads. The composite sheet is then transported to the second airlaid forming area, where a second airlaid nonwoven layer is deposited overlying the previously deposited airlaid layer. This process is repeated until the desired amount of airlaid layers are deposited onto the composite sheet. The resulting composite sheet may then be stabilized with a heated roller that was heated to a temperature of 80 to 180° C. The composite sheet was then transported to, and passed through, a first heated oven, which was maintained at a temperature from about 120 to 165° C. At higher speeds, it may be desirable to increase the oven temperature. The temperature of the first oven was selected to soften and melt the non-cellulose fibers of both the airlaid layers as well as the fluid acquisition layer (e.g., ATB layer) so that the fibers melt and flow together to form a coherent composite sheet.

Prior to passing through the oven, the composite sheet was transported to a coating station at which point a coating layer comprised of a latex formulation was deposited onto the surface of the outermost airlaid to form a coating layer. The composite sheet was then heated in an oven to dry and cure the latex coating. The oven was maintained at a temperature from about 120 to 150° C. Optionally, the composite sheet may further be dried in a third oven. The resulting basis weight for

Inventive Example 1

Inventive Example 1 was prepared by depositing 2 airlaid layers onto a previously prepared fabric of ATB-1. The airlaid layers comprised a homogenous fiber mixture of Pulp-1 fibers and PE/PET-1 fibers. Following deposition of the two airlaid layers, a coating of the Latex formulation was applied to the surface of the outermost airlaid layer. The composite sheet material was then successively passed through a series of ovens to bond the fibers to each other, and to dry and cure the Latex formulations. The dried add-on weight of the Latex layer was 3 weight percent, based on the total dry weight of Inventive Example 1. The resulting composite sheet had a basis weight of 80 g/m$^2$.

Comparative Example 1

Comparative Example 1 was prepared by depositing 2 airlaid layers onto a previously prepared fabric of ATB-1. The airlaid layers comprised a homogenous fiber mixture of Pulp-2 fibers and PE/PET-1 fibers. A latex formulation of the Latex was applied to the Comparative Example 1 as an as dried amount of 3 weight %, based on total weight of the composite fabric. The fabric was dried in one or more ovens at temperatures from 150 to 160° C.

In Table 1, below, samples of Comparative Example 1 and Inventive Example 1 were obtained and evaluated for fluid management properties. As can be seen in the table, the fluid management properties were quite comparable despite a percent decrease in thickness of 34% in the sample having bamboo derived staple fibers in lieu of fibers comprising conventional wood pulp. For instance, Inventive Example 1 while having a thickness that was decreased by 34% in comparison to Comparative Example 1 only exhibited a decrease of 9% with respect to fluid retention. This shows that despite being significantly thinner, the inventive composite sheet exhibits good fluid retention properties, which is particularly desirable in absorbent articles.

TABLE 1

Comparison of Fluid Management Properties

| Example No. | Basis weight (gsm) | Caliper (mm) | Fluid retention (g/g) | Acquisition time 1$^{st}$ Insult (s) | Acquisition time 2$^{nd}$ Insult (s) | Acquisition time 3$^{rd}$ Insult (s) | Rewet (g) |
|---|---|---|---|---|---|---|---|
| Comparative Example 1 | 80 | 2.05 | 8.8 | 0.8 | 1.1 | 1.2 | 0.07 |
| Inventive Example 1 | 80 | 1.35 | 8 | 0.9 | 1.3 | 1.6 | 0.09 |

In Tables 2-4, below, the wicking properties and stiffness of the inventive composite sheet material was compared to a similar composite sheet material that did not include bamboo derived staple fibers in the airlaid layers. The results in Tables 2 and 3 were obtained by taking six different samples of the Inventive and Comparative composite sheets and then measuring the noted properties. In Table 4, the average results from each measurement were compared to determine the percent increase/decrease as well as the percent difference between the inventive and comparative composite sheet.

TABLE 2

Properties of Comparative Example 1

| Measurement | 1 | 2 | 3 | 4 | 5 | 6 | Average |
|---|---|---|---|---|---|---|---|
| Caliper (Mm) | 2.06 | 2.13 | 2.21 | 2.16 | 2.20 | 2.20 | 2.16 |
| Vertical Wicking Height (mm) | 20 | 22 | 21 | 23 | 24 | 23 | 22 |

TABLE 2-continued

Properties of Comparative Example 1

| Measurement | 1 | 2 | 3 | 4 | 5 | 6 | Average |
|---|---|---|---|---|---|---|---|
| Wicking Rate (mm/15 sec) | 21 | 24 | 19 | 20 | 18 | 18 | 20 |
| MD stiffness (mN/cm) | 58 | 51 | 46 | 60 | 56 | 52 | 54 |
| CD stiffness (mN/cm) | 16 | 16 | 18 | 19 | 20 | 18 | 18 |

TABLE 3

Properties of Inventive Example 1

| Measurement | 1 | 2 | 3 | 4 | 5 | 6 | Average |
|---|---|---|---|---|---|---|---|
| Caliper (Mm) | 1.32 | 1.20 | 1.30 | 1.25 | 1.47 | 1.39 | 1.32 |
| Vertical Wicking Height (mm) | 45 | 49 | 44 | 50 | 42 | 52 | 47 |
| Wicking Rate (mm/15 sec) | 32 | 35 | 33 | 32 | 35 | 34 | 34 |
| MD stiffness (mN/cm) | 26 | 29 | 33 | 40 | 36 | 39 | 34 |
| CD stiffness (mN/cm) | 8 | 8 | 9 | 9 | 10 | 11 | 9 |

In Table 4, below, the average results for Comparative Example 1 and Inventive Example 1 are compared by measuring the percent differences for the average of each measurement.

TABLE 4

Comparison of Average results for Tables 2 and 3

| Test Measurement | Percent Change (%) | Percent Difference (%) |
|---|---|---|
| Caliper | 36.8 Decrease | 48.3 |
| Vertical Wicking Height | 126.1 Increase | 77.3 |
| Wicking Rate | 88.9 Increase | 61.5 |
| MD Stiffness | 25% Decrease | 28.6 |
| CD Stiffness | 38.9 Decrease | 48.3 |

Percent Change = $(V_2 - V_1/|V_2| \times 100$

Percent Difference = $|V_1 - V_2|/[(V_1 + V_2)/2] \times 100$

As can be seen from the above, the wicking height and rate most showed significant improvement in comparison to the comparative composite sheet. This indicates that the inventive composite sheet would be expected to provide good fluid management properties in an absorbent article.

In addition, the inventive composite sheet material exhibited a reduction in CD stiffness of approximately 40% and a reduction in MD stiffness of 25% in comparison to the comparative composite sheet, which did not include the bamboo derived staple fibers. This further illustrates that absorbent articles comprising the inventive composite sheet material, and hence, the inventive airlaid nonwoven, would be expected to provide improvements with respect to fluid management properties, as evidenced by the increases in wicking rates and wicking heights, while at the same time providing a material have reduced stiffness. Advantageously, the reduced stiffness and reduced thickness may help provide an absorbent article having more flexibility, which in turn, provides an increased level of comfort and discreetness to the wearer.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An absorbent core for an absorbent article, the core comprising 2 to 10 separately formed airlaid layers consisting of staple fibers in which 50 to 100 percent of the staple fibers, based on the total weight of the absorbent core, are bamboo derived staple fibers, and wherein the absorbent core exhibits the following:

a decrease in thickness from 10 to 60% in comparison to a similar absorbent core in which the similar absorbent core comprises staple fibers derived from conventional wood pulp fibers in lieu of the bamboo derived staple fibers;

a decrease in machine direction (MD) stiffness from 10 to 50% in comparison to a similar absorbent core in which the similar absorbent core comprises staple fibers derived from conventional wood pulp fibers in lieu of the bamboo derived staple fibers; and an increase in wicking rate that is from 40 to 120% in comparison to a similar absorbent core in which the similar absorbent core comprises staple fibers derived from conventional wood pulp fibers in lieu of the bamboo derived staple fibers.

2. The absorbent core of claim 1, wherein the airlaid layers comprise a blend of bamboo derived staple fibers and non-cellulose staple fibers.

3. The absorbent core of claim 2, wherein the non-cellulose staple fibers comprises fibers derived from synthetic polymers, fibers derived from bio-based polymers, combinations of fibers derived from synthetic polymers and bio-based polymers, and blends of polymers derived from synthetic polymers and bio-based polymers.

4. The absorbent core of claim 2, wherein the non-cellulose staple fibers are bicomponent staple fibers having a polyethylene sheath and a polypropylene or polyethylene terephthalate core, and mixtures thereof.

5. The absorbent core of claim 2, wherein the absorbent core comprises three airlaid layers.

6. The absorbent core of claim 2, wherein the bamboo derived staple fibers have an average length from about 0.8 to 4.5 mm, and an average width from about 12 to 22 microns.

7. The absorbent core of claim 2, wherein the bamboo derived staple fibers have a length to width ratio that is from about 60 to 120.

8. The absorbent core of claim 2, wherein the absorbent core has a basis weight ranging from about 25 to 400 gsm and a thickness ranging from about 0.4 to 4 mm.

9. The absorbent core of claim 1, wherein the absorbent core comprises a tissue layer.

10. The absorbent core of claim 9, wherein the airlaid layers of the absorbent core are sandwiched between a pair of tissue layers.

11. The absorbent core of claim 1, wherein the absorbent core further comprises:

a first layer of fibers bonded together to form a coherent web; and an airlaid nonwoven layer overlying the first layer, the airlaid nonwoven layer comprising a blend of bamboo derived staple fibers, the airlaid nonwoven layer comprising a first surface disposed towards, and thermally bonded, to a surface of the first layer, and a second surface defining an outer surface of the absorbent core.

12. The absorbent core of claim 11, wherein the first layer is selected from the group consisting of spunbond nonwoven, meltblown nonwoven, spunlace nonwoven, carded nonwoven, airlaid nonwoven, a spunbond-meltblown-spunbond composite (SMS), cellulosic tissue paper, film, and combinations thereof.

13. The absorbent core of claim 10, wherein the tissue layers comprise tissue derived from bamboo fibers, conventional wood pulp fibers, and mixtures thereof.

14. The absorbent core of claim 1, wherein the absorbent core comprises a bio-based polymer layer comprising carboxy methyl cellulose.

15. An absorbent core for an absorbent article, the absorbent core comprising two or more separately formed airlaid layers consisting of staple fibers and optionally a latex material, wherein the staple fibers include bamboo derived staple fibers, the bamboo derived staple fibers being present in an amount from 75 to 100 weight percent, based on the total weight of the absorbent core, and wherein the bamboo derived staple fibers are bonded to each other via a latex material or via hydrogen bonding, and wherein the absorbent core exhibits the following:

a decrease in thickness from 10 to 60% in comparison to a similar absorbent core in which the similar absorbent core comprises staple fibers derived from conventional wood pulp fibers in lieu of the bamboo derived staple fibers;

a decrease in machine direction (MD) stiffness from 10 to 50% in comparison to a similar absorbent core in which the similar absorbent core comprises staple fibers derived from conventional wood pulp fibers in lieu of the bamboo derived staple fibers; and an increase in wicking rate that is from 40 to 120% in comparison to a similar absorbent core in which the similar absorbent core comprises staple fibers derived from conventional wood pulp fibers in lieu of the bamboo derived staple fibers.

16. The absorbent core of claim 15, wherein the absorbent core comprises substantially no non-cellulose staple fibers.

17. The absorbent core of claim 15, wherein the absorbent core comprises a tissue layer.

18. The absorbent core of claim 15, wherein said two or more separately formed airlaid layers are sandwiched between a pair of tissue layers.

19. The absorbent core of claim 18, wherein the tissue layers comprise tissue derived from bamboo fibers, conventional wood pulp fibers, and mixtures thereof.

20. The absorbent core of claim 15, wherein the bamboo derived staple fibers have an average length from about 0.8 to 4.5 mm, and an average width from about 12 to 22 microns.

21. The absorbent core of claim 15, wherein the bamboo derived staple fibers having a length to width ratio that is from about 60 to 120.

* * * * *